United States Patent
Krueger et al.

(10) Patent No.: US 9,456,976 B2
(45) Date of Patent: *Oct. 4, 2016

(54) HAIR TREATMENT COMPOSITIONS COMPRISING SELECTED UV FILTERS AND SELECTED COMPLEXES OF ACIDIC PROTEIN HYDROLYSATES AND BASIC FATTY ACID AMIDOAMINES

(71) Applicant: Henkel AG & Co. KGaA, Duesseldorf (DE)

(72) Inventors: Marcus Krueger, Ellerhoop (DE); Jorg Kahre, Leichlingen (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/615,528

(22) Filed: Feb. 6, 2015

(65) Prior Publication Data
US 2015/0150773 A1 Jun. 4, 2015

Related U.S. Application Data

(63) Continuation of application No. PCT/EP2013/064768, filed on Jul. 12, 2013.

(30) Foreign Application Priority Data

Aug. 9, 2012 (DE) ......................... 10 2012 214 151

(51) Int. Cl.
| | | |
|---|---|---|
| A61Q 5/12 | (2006.01) | |
| A61K 8/64 | (2006.01) | |
| A61K 8/42 | (2006.01) | |
| A61Q 5/02 | (2006.01) | |
| A61Q 17/04 | (2006.01) | |

(52) U.S. Cl.
CPC . *A61K 8/64* (2013.01); *A61K 8/42* (2013.01); *A61K 8/645* (2013.01); *A61Q 5/02* (2013.01); *A61Q 5/12* (2013.01); *A61Q 17/04* (2013.01)

(58) Field of Classification Search
None
See application file for complete search history.

(56) References Cited

U.S. PATENT DOCUMENTS

| | | | |
|---|---|---|---|
| 2005/0227880 A1 | 10/2005 | Shiloach et al. | |
| 2006/0083704 A1 | 4/2006 | Torgerson | |
| 2008/0025939 A1* | 1/2008 | Cassier | A61K 8/447 424/70.5 |
| 2009/0169644 A1* | 7/2009 | Goddinger | A61K 8/922 424/642 |
| 2009/0304620 A1* | 12/2009 | Schulze zur Wiesche | A61K 8/84 424/70.12 |
| 2010/0028272 A1* | 2/2010 | Knappe | A61K 8/8152 424/47 |
| 2011/0033407 A1* | 2/2011 | Krueger | A61K 8/97 424/70.9 |

FOREIGN PATENT DOCUMENTS

WO     2012/084339 A2     6/2012

OTHER PUBLICATIONS

Vegetamide 18 MEA product brochure (Mar. 2011).*
PCT International Search Report (PCT/EP2013/064768) dated May 8, 2014.
Database GNPD [Online] MINTEL, "Styling Gel", XP002727937, Database accession No. 569844, Aug. 2006.
Kobayashi, "Hair Conditioning Ingredients Developed with Focusing on Hair Surface Structure", XP002727880, SOFW-Journal, vol. 138, pp. 28-36, 2012.

* cited by examiner

*Primary Examiner* — Jyothsna Venkat
(74) *Attorney, Agent, or Firm* — David K. Benson

(57) ABSTRACT

The present invention relates to hair treatment agents that include a synergistic combination of selected UV filters and selected complexes of acid protein hydrolysates and basic fatty acid amidoamines.

16 Claims, No Drawings

HAIR TREATMENT COMPOSITIONS COMPRISING SELECTED UV FILTERS AND SELECTED COMPLEXES OF ACIDIC PROTEIN HYDROLYSATES AND BASIC FATTY ACID AMIDOAMINES

FIELD OF THE INVENTION

The present invention generally relates to hair treatment agents that include UV filters and complexes of acid protein hydrolysates and basic fatty acid amidoamines.

BACKGROUND OF THE INVENTION

There is a need to further improve hair care products and to give them further advantageous properties. In particular, a care complex should be provided that can ideally also be used in conjunction with oxidizing agents and surfactant agents.

Environmental influences and oxidative hair treatments often lead to poorer combability of dry and wet hair. Furthermore, hair shine and moisture balance are adversely influenced by the attack on the external structure of the keratinic fibers. A further consequence of repeated treatments of keratinic fibers with surfactant and/or oxidative agents is a high degree of grease buildup in the keratinic fibers as well as a strong tendency to the increased formation of dandruff.

It is therefore desirable to reduce the side-effects of environmental influences and of oxidative and surfactant hair treatments, preferably during the actual oxidative or surfactant hair treatment but also after the oxidative or surfactant hair treatment, without adversely affecting the efficiency of the oxidative or surfactant cosmetic, in particular with regard to color intensity, color fastness, lightening capacity or waving effect. It is also desirable to prevent grease buildup in the keratinic fibers and the formation of dandruff. It is further desirable to provide a 2-in-1 product for the oxidative treatment of keratin-containing fibers, in particular human hair, which also imparts in one application step an effective protection of the fibers against environmental influences such as UV protection.

Furthermore, other desirable features and characteristics of the present invention will become apparent from the subsequent detailed description of the invention and the appended claims, taken in conjunction with the accompanying drawings and this background of the invention.

BRIEF SUMMARY OF THE INVENTION

A hair treatment agent includes—relative to its weight—at least one selected complex of an acid protein hydrolysate and a basic fatty acid amidoamine in a total amount from 0.01 to 10.0 wt. %, relative to the total composition; and at least one UV filter in a total amount from 0.01 to 15.0 wt. %, relative to the total composition.

A particular hair treatment agent includes—relative to its weight—at least one cetearamidoethyl diethonium hydrolyzed protein in a total amount from 0.1 to 10.0 wt. %, relative to the total composition; and at least one UV filter in a total amount from 0.01 to 15.0 wt. %, relative to the total composition.

DETAILED DESCRIPTION OF THE INVENTION

The following detailed description of the invention is merely exemplary in nature and is not intended to limit the invention or the application and uses of the invention. Furthermore, there is no intention to be bound by any theory presented in the preceding background of the invention or the following detailed description of the invention.

Fatty acid amidoamines and protein hydrolysates are chemical compounds which are known in principle and are already used in hair care agents as ingredients in their own right. UV filters are likewise known in hair treatment agents. They are frequently used to protect the fibers against UV radiation. However, these known compositions cannot solve the problems in a satisfactory manner. Where reference is made below to the active agent complex, this relates to the required ingredients a) and b) contained in the hair treatment agents according to the invention.

The active agent complex according to the invention leads to an improvement in finish, to an improvement in shine, to an improvement in moisture balance and to protection against the destructuring of keratin-containing fibers, in particular human hair, by UV radiation and most particularly to protection against oxidative damage, in particular to the maintenance of hair growth, the prevention of hair loss and the prevention of grease buildup in the keratinic fibers as well as to an increase in the washing resistance of colored keratinic fibers. The present invention therefore firstly provides a hair treatment agent that includes—relative to its weight— a) at least one selected complex of an acid protein hydrolysate and a basic fatty acid amidoamine in a total amount from 0.01 to 10.0 wt. %, and
b) at least one UV filter in a total amount from 0.01 to 15.0 wt. %, relative to the total composition.

In a preferred embodiment of the present invention the cosmetic agents serve to treat keratinic fibers, in particular human hair. Preferred agents according to the invention are therefore shampoos, hair coloring agents, conditioning agents or hair tonics, for example.

Feel is defined as the tactility of a group of fibers, the person skilled in the art feeling and assessing the fullness and softness qualities of the group of fibers by sensory means.

Shaping is understood to be the ability to change the shape of a group of previously treated keratin-containing fibers, in particular human hair. In hair cosmetics this is also referred to as styling ability.

Maintenance of the natural growth of keratinic fibers is understood to mean that the influences on natural hair growth through cosmetic hair treatments as described above, in particular through oxidative hair treatments, are balanced out and that there are no or at most slight effects on the natural growth of the keratinic fibers in terms of growth in diameter, growth in length and/or in terms of hair fullness.

According to the invention an oxidative hair treatment is defined as the action of an oxidative cosmetic agent that includes at least one oxidizing agent in a cosmetic carrier on hair.

The hair treatment agent that includes the active agent complex according to the invention is preferably used immediately before, during or after the oxidative or surfactant hair treatment. Within the meaning of the invention, immediately before the oxidative or surfactant hair treatment is understood to mean an application which is followed directly by the oxidative or surfactant hair treatment, wherein the hair treatment agent that includes the active agent complex according to the invention was first rinsed from the hair or was preferably left on the hair and the hair is preferably still wet.

Within the meaning of the invention, after the oxidative or surfactant hair treatment is understood to mean an application which either follows on directly from the oxidative or surfactant hair treatment, wherein the hair treatment agent that includes the active agent complex according to the invention is applied to the preferably still wet, towel-dry hair after rinsing off the oxidative or surfactant agent, or is applied to dry or wet hair only after several hours or days. In both cases the hair treatment agent according to the invention can be rinsed out again after a contact time from a few seconds up to 45 minutes or can be left entirely on the hair.

The effect of the hair treatment agent according to the invention develops during the actual oxidative or surfactant hair treatment and surprisingly continues even after the hair treatment agent according to the invention has been thoroughly washed out.

The active agent complex according to the invention is preferably used in a cosmetic carrier. The cosmetic carriers can in particular be aqueous or aqueous-alcoholic. An aqueous cosmetic carrier includes at least 50 wt. % of water. Within the meaning of the present invention aqueous-alcoholic cosmetic carriers are understood to be aqueous solutions that include 3 to 70 wt. % of a $C_1$-$C_6$ alcohol, in particular methanol, ethanol or propanol, isopropanol, butanol, isobutanol, tert-butanol, n-pentanol, isopentanols, n-hexanol, isohexanols, glycol, glycerol, 1,2-pentanediol, 1,5-pentanediol, 1,2-hexanediol or 1,6-hexanediol. The agents according to the invention can additionally include further organic solvents, such as for example methoxybutanol, benzyl alcohol, ethyl diglycol or 1,2-propylene glycol. All water-soluble organic solvents are preferred here.

Constituent a) of the active agent complex according to the invention is an ionic complex consisting of an acid protein hydrolysate and a basic fatty acid amidoamine. In the present invention an acid protein hydrolysate is understood to be preferably a plant-based protein hydrolysate. The protein hydrolysate component can of course come from any protein source. Plant-based protein hydrolysates, such as soy, almond, pea, moringa, potato and wheat protein hydrolysates, are preferred. Collagen hydrolysates of fish or algae and protein hydrolysates of mussels or pearl hydrolysates are likewise included according to the invention. It is however essential to the present invention that the proportion of acid amino acids in the hydrolysate is at least 10 wt. %, preferably 20 wt. %, particularly preferably 30 wt. % and most highly preferably 40 wt. %. Protein hydrolysates which meet this condition form the ionic complexes according to the invention consisting of an acid protein hydrolysate and a basic fatty acid amidoamine of the present invention. According to the invention protein hydrolysates based on elastic, collagen, keratin, silk and milk protein are also possible, albeit not preferred.

Any fatty acid amidoamine having a chain length from 8 to 40 carbon atoms in the chain is possible as fatty acid amidoamines. The fatty acid amidoamines can be saturated or unsaturated, straight-chain or branched. The fatty acid amidoamines according to the invention preferably satisfy the following structure:

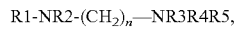
R1-NR2-(CH$_2$)$_n$—NR3R4R5, in which R1 denotes a linear or branched, saturated or unsaturated acyl residue having 8 to 40 C atoms in the chain, R2 denotes a C1 to C4 alkyl residue or hydrogen, R3, R4 and R5 independently of one another denote hydrogen, a methyl residue or a C2 to C4 alkyl residue, n denotes an integer selected from 1, 2, 3, 4 or 5. R2 particularly preferably denotes a methyl or ethyl residue, n=2 and R3=R4=methyl or ethyl and R5 denotes hydrogen. R1 preferably denotes one of the residues caprinoyl, lauroyl, myristoyl, palmitoyl, stearoyl, oleoyl, linoloyl, arachinoyl, cetyloyl, behenoyl, eicosanoyl and/or 18-methyleicosanoyl.

No anion is shown in the above structure. This anion is formed by an acid group of the protein hydrolysate. As the acid protein hydrolysates according to the invention can have a plurality of acid groups, a plurality of the structures of the fatty acid amidoamines as described above are ionically bound correspondingly to the acid groups.

The carboxy-terminal end of the acid protein hydrolysates together with the cationic or cationizable C8 to C40 fatty acid amidoamine forms an ionic complex. Examples of such compounds are commercially obtainable under the INCI name cetearamidoethyl diethonium hydrolyzed protein based on wheat or rice, under the names Vegetamid® 18MEA R (cetearamidoethyl diethonium hydrolyzed rice) or Vegetamid® 18MEA G (cetearamidoethyl diethonium hydrolyzed wheat) from Seiwa Kasei.

The ionic complexes of an acid protein hydrolysate and a fatty acid amidoamine according to the invention are included in the compositions according to the invention in an amount from 0.01 to 10.0 wt. %, preferably from 0.01 to 7.5 wt. %, particularly preferably from 0.1 to 5.0 wt. %, relative to the total composition.

As the second essential ingredient b) a UV filter is included in the hair treatment agents. UV filters can be present in oil-soluble form, in water-soluble form or in solid form as a pigment. Moreover, UV filters are divided into UVA and UVB filters, according to their optimum efficacy.

Examples of oil-soluble substances that can be cited include:

3-benzylidene camphor, for example 3-(4-methylbenzylidene)camphor;

4-aminobenzoic acid derivatives, preferably 4-(dimethylamino)benzoic acid-2-ethylhexyl ester, 4-(dimethylamino)benzoic acid-2-octyl ester and 4-(dimethylamino) benzoic acid amyl ester;

esters of cinnamic acid, preferably 4-methoxycinnamic acid-2-ethylhexyl ester, 4-methoxycinnamic acid propyl ester, 4-methoxycinnamic acid isoamyl ester, 2-cyano-3-phenylcinnamic acid-2-ethylhexyl ester (octocrylene);

esters of salicylic acid, preferably salicylic acid-2-ethylhexyl ester, salicylic acid-4-isopropylbenzyl ester, salicylic acid homomenthyl ester;

derivatives of benzophenone, preferably 2-hydroxy-4-methoxybenzophenone, 2-hydroxy-4-methoxy-4'-methylbenzophenone, 2,2'-dihydroxy-4-methoxybenzophenone;

esters of benzalmalonic acid, preferably 4-methoxybenzomalonic acid di-2-ethylhexyl ester;

triazine derivatives, such as for example 2,4,6-trianilino-(p-carbo-2'-ethyl-1'-hexyloxy)-1,3,5-triazine and octyl triazone;

propane-1,3-diones, such as for example 1-(4-tert-butylphenyl)-3-(4'-methoxyphenyl)propane-1,3-dione.

Suitable water-soluble substances include:

2-phenylbenzimidazole-5-sulfonic acid and alkali, alkaline-earth, ammonium, alkyl ammonium, alkanol ammonium and glucammonium salts thereof;

sulfonic acid derivatives of benzophenones, preferably 2-hydroxy-4-methoxybenzophenone-5-sulfonic acid and salts thereof;

sulfonic acid derivatives of 3-benzylidene camphor, such as for example 4-(2-oxo-3-bornylidene methyl)benzenesulfonic acid and 2-methyl-5-(2-oxo-3-bornylidene)sulfonic acid and salts thereof.

Derivatives of benzoyl methane are suitable in particular as typical UV-A filters, such as for example 1-(4'-tert-butylphenyl)-3-(4'-methoxyphenyl)propane-1,3-dione or 1-phenyl-3-(4'-isopropylphenyl) propane-1,3-dione. The UV-A and UV-B filters can naturally also be used in mixtures.

In addition to the cited soluble substances, insoluble pigments, in particular finely dispersed metal oxides or salts, are suitable for this purpose, such as for example titanium dioxide, zinc oxide, iron oxide, aluminum oxide, cerium oxide, zirconium oxide, silicates (talc), barium sulfate and zinc stearate. These pigments are preferred according to the invention, in particular as a constituent of a mixture of several structurally different UV filters. The particles should have an average diameter of less than 100 nm, preferably between 5 and 50 nm and in particular between 15 and 30 nm. They can have a spherical form, but such particles having an ellipsoid form or other form deviating from the spherical shape can also be used.

The total amount of UV filter substances in the compositions according to the invention, relative to the total composition, is in each case 0.01 to 15.0 wt. %, preferably 0.01 to 10.0 wt. %, more preferably 0.1 to 10.0 wt. %, particularly preferably 0.2 to 10.0 wt. % and most highly preferably 0.3 to 10.0 wt. %.

In a particularly preferred embodiment of the present invention further selected quaternary ammonium compounds are preferably used with the aforementioned required ingredients. In principle quaternary ammonium compounds are monomeric cationic or amphoteric ammonium compounds, monomeric amines, amino amides, polymeric cationic ammonium compounds and polymeric amphoteric ammonium compounds. Of this large number of possible quaternary ammonium compounds, the following groups have proved to be particularly suitable and are used individually in each case in an amount from 0.1 to 15.0 wt. %. The amount remains within this range even if a mixture of different compounds of the quaternary ammonium compounds is used.

Cationic surfactants of formula (Tkat1-1) form the first group of cationic surfactants.

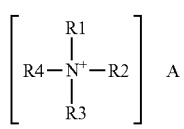

(Tkat1)

In the formula (Tkat1) R1, R2, R3 and R4 independently of one another each denote hydrogen, a methyl group, a phenyl group, a benzyl group, a saturated, branched or unbranched alkyl residue having a chain length of 8 to 30 carbon atoms, which can optionally be substituted with one or more hydroxyl groups. A denotes a physiologically acceptable anion, for example halides such as chloride or bromide and methosulfates.

Examples of compounds of formula (Tkat1) are lauryl trimethylammonium chloride, cetyl trimethylammonium chloride, cetyl trimethylammonium bromide, cetyl trimethylammonium methosulfate, dicetyl dimethylammonium chloride, tricetyl methylammonium chloride, stearyl trimethylammonium chloride, distearyl dimethylammonium chloride, lauryl dimethyl benzylammonium chloride, behenyl trimethylammonium chloride, behenyl trimethylammonium bromide, behenyl trimethylammonium methosulfate.

Esterquats according to formula (Tkat2) form a preferred group.

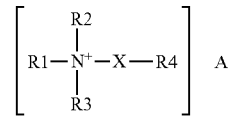

(Tkat2)

Here residues R1, R2 and R3 are each independent of one another and can be the same or different. Residues R1, R2 and R3 denote:
  a branched or unbranched alkyl residue having 1 to 4 carbon atoms, which can include at least one hydroxyl group, or
  a saturated or unsaturated, branched or unbranched or a cyclic saturated or unsaturated alkyl residue having 6 to 30 carbon atoms, which can include at least one hydroxyl group, or
  an aryl or alkaryl residue, for example phenyl or benzyl, the residue (—X—R4), with the proviso that at most 2 of residues R1, R2 or R3 can denote this residue.
The residue —(X—R4) is included at least 1 to 3 times.
Here X denotes:
1) —$(CH_2)_n$— where n=1 to 20, preferably n=1 to 10 and particularly preferably n=1 to 5, or
2) —$(CH_2—CHR5-O)_n$— where n=1 to 200, preferably 1 to 100, particularly preferably 1 to 50, and particularly preferably 1 to 20 with R5 denoting hydrogen, methyl or ethyl,
3) a hydroxyalkyl group having one to four carbon atoms, which can be branched or unbranched and which can include at least one and at most three hydroxyl groups. Examples are: —$CH_2OH$, —$CH_2CH_2OH$, —CHOHCHOH, —$CH_2CHOHCH_3$, —$CH(CH_2OH)_2$, —$COH(CH_2OH)_2$, —$CH_2CHOHCH_2OH$, —$CH_2CH_2CH_2OH$ and hydroxybutyl residues,
and R4 denotes:
1) R6-O—CO—, in which R6 is a saturated or unsaturated, branched or unbranched or a cyclic saturated or unsaturated alkyl residue having 6 to 30 carbon atoms, which can include at least one hydroxyl group and which can optionally also be ethoxylated with 1 to 100 ethylene oxide units and/or 1 to 100 propylene oxide units, or
2) R7-CO—, in which R7 is a saturated or unsaturated, branched or unbranched or a cyclic saturated or unsaturated alkyl residue having 6 to 30 carbon atoms, which can include at least one hydroxyl group and which can optionally also be ethoxylated with 1 to 100 ethylene oxide units and/or 1 to 100 propylene oxide units,
and A denotes a physiologically acceptable organic or inorganic anion and is defined here also as a representative of all structures described below. The anion of all cationic compounds that are described here is selected from the halide ions, fluoride, chloride, bromide, iodide, sulfates of the general formula $RSO_3^-$, in which R has the meaning of saturated or unsaturated alkyl residues having 1 to 4 carbon atoms, or anionic residues of organic acids such as maleate, fumarate, oxalate, tartrate, citrate, lactate or acetate.

Such products are sold under the trademarks Rewoquat®, Stepantex®, Dehyquart®, Armocare® and Akypoquat® for example. The products Armocare® VGH-70, Dehyquart® F-75, Dehyquart® C-4046, Dehyquart® L80, Dehyquart® F-30, Dehyquart® AU-35, Rewoquat® WE18, Rewoquat® WE38 DPG, Stepantex® VS 90 and Akypoquat® 131 are examples of these esterquats.

Further compounds of formula (Tkat1-2) that are particularly preferred according to the invention are included in formula (Tkat2.1), cationic betaine esters.

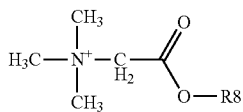
(Tkat2.1)

R8 corresponds in its meaning to R7.

The esterquats with the trade names Armocare® VGH-70 and also Dehyquart® F-75, Dehyquart® L80, Stepantex® VS 90 and Akypoquat® 131 are particularly preferred.

In preferred agents according to the invention cationic surfactants of formula (bI) are used within relatively narrow quantity ranges, such that preferred hair treatment agents according to the invention are characterized in that they include 0.1 to 15 wt. %, preferably 0.5 to 10 wt. %, more preferably 1 to 10 wt. %, still more preferably 1.5 to 10 wt. % and in particular 2 to 5 wt. % of at least one compound of general formula (I),

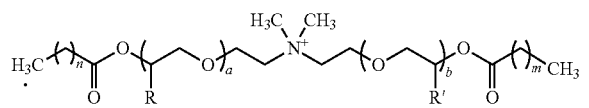
Formula (I)

in which n and m independently of one another denote integers between 5 and 40, with the proviso that n+m≥38; particularly preferably n=m; most highly preferably n=m=20.

a and b independently of one another denote integers between 1 and 10; particularly independently of one another they denote 1, 2, 3, 4 or 5, wherein preferably a+2≥b≥a–2 and most highly preferably a=b=3.

R and R' are independently of one another selected from —H and —CH₃; preferably R=R', such that preferably either PEG or PPG diesterquats are used; most particularly preferably R=R'=—CH₃.

X⁻ is a physiologically acceptable anion, a halide such as chloride, bromide or iodide, toluenesulfonate, methosulfate, etc., and particularly preferably methosulfate.

In particular if one of the compounds of formula (I) as described above is used, it has been found that the care effects of the agents according to the invention can be further increased and in particular the stability of the agents further improved if the agents include certain acylated diamines in addition to the compound(s) of formula (I).

Preferred hair treatment agents according to the invention are therefore characterized in that they additionally include 0.1 to 10 wt. % of at least one compound of formula (II)

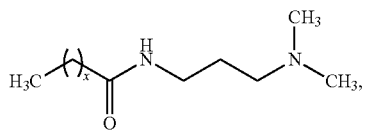
(II)

in which x denotes 18, 19, 20, 21, 22, 23 or 24.

Compounds of formula (II) with n=20 are particularly preferred. Most highly preferred agents according to the invention are characterized in that they always include a compound of formula (I) together with a compound of general formula (II).

Quaternary imidazoline compounds are a further group. Formula (Tkat2) below shows the structure of these compounds.

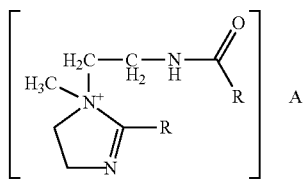
(Tkat2)

The residues R independently of one another each denote a saturated or unsaturated, linear or branched hydrocarbon residue having a chain length of 8 to 30 carbon atoms. The preferred compounds of formula (Tkat2) each include the same hydrocarbon residue for R. The chain length of the residues R is preferably 12 to 21 carbon atoms. A denotes an anion as described above. Particularly suitable examples according to the invention are available for example under the INCI names Quaternium-27, Quaternium-72, Quaternium-83 and Quatemium-91. Quatemium-91 is most highly preferred according to the invention.

Fatty acid amides of general formula (I) are likewise preferred active agents of group b),

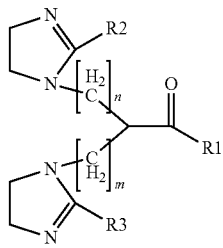
Formula (I)

in which R1, R2 and R3 independently of one another denote a linear branched or unbranched C6 to C30, preferably C8 to C24, more preferably C12 to C22 and most highly preferably C12 to C18 alkyl or alkenyl group. R1 to R3 preferably denote capryl, caprylyl, octyl, nonyl, decanyl, lauryl, myristyl, cetyl, stearyl, isostearyl, oleyl, behenyl or arachidyl. Furthermore, R2 is particularly preferably equal to R3 and most highly preferably R1 is equal to R2 which is equal to R3. The letters n and m independently of one another denote integers from 1 to 10, preferably 2 to 6 and most highly preferably 2, 3 and/or 4, wherein most highly preferably n=m. Most highly preferably, R1 is equal to R2 which is equal to R3 and is selected from capryl, caprylyl, octyl, nonyl, decanyl, lauryl, myristyl, cetyl, stearyl, isostearyl, oleyl, behenyl or arachidyl and n=m=2. Most preferably, R1=R2=R3 and is selected from lauryl, myristyl, cetyl, stearyl, isostearyl, oleyl, behenyl or arachidyl, of which cetyl, stearyl, isostearyl, oleyl or behenyl are particularly preferred, and n=m=2. The most preferred compound of formula (I) is the one bearing the INCI name Bis-Ethyl (isostearylimidazoline) Isostearamide. This last compound is commercially available from Croda under the trade name Keradyn® HH.

In a particularly preferred embodiment of the invention the agents according to the invention include furthermore at least one amine and/or cationized amine, in particular an amidoamine and/or a cationized amidoamine of the following structural formulas:

(Tkat3)

in which R1 denotes an acyl or alkyl residue having 6 to 30 C atoms, which can be branched or unbranched, saturated or unsaturated, and wherein the acyl residue and/or alkyl residue can include at least one OH group, and R2, R3 and R4 in each case independently of one another denote 1) hydrogen or 2) an alkyl residue having 1 to 4 C atoms, which can be the same or different, saturated or unsaturated, and 3) a branched or unbranched hydroxyalkyl group having 1 to 4 carbon atoms with at least one and at most three hydroxyl groups, for example —$CH_2OH$, —$CH_2CH_2OH$, —CHOHCHOH, —$CH_2CHOHCH_3$, —$CH(CH_2OH)_2$, —$COH(CH_2OH)_2$, —$CH_2CHOHCH_2OH$, —$CH_2CH_2CH_2OH$ and hydroxybutyl residues, and A denotes an anion as described above, and n denotes an integer between 1 and 10.

A composition in which the amine and/or the quaternized amine according to the general formula (Tkat3) is an amidoamine and/or a quaternized amidoamine in which R1 denotes a branched or unbranched, saturated or unsaturated acyl residue having 6 to 30 C atoms, which can include at least one OH group, is preferred. A fatty acid residue from oils and waxes, in particular from natural oils and waxes, is preferred here. Suitable examples include lanolin, beeswax or candelilla wax.

Also preferred are amidoamines and/or quaternized amidoamines in which R2, R3 and/or R4 in formula (Tkat3) denote a residue according to general formula $CH_2CH_2OR5$, in which R5 can have the meaning of alkyl residues having 1 to 4 carbon atoms, hydroxyethyl or hydrogen. The preferred value of n in the general formula (Tkat8) is an integer between 2 and 5.

The alkyl amidoamines can be present as is and can also be converted into a quaternary compound in the composition by protonation in a correspondingly acid solution. Cationic alkyl amidoamines are preferred according to the invention.

Examples of such commercial products according to the invention are Witcamine® 100, Incromine® BB, Mackine® 401 and other Mackine® types, Adogen® S18V, and as permanently cationic amino amines: Rewoquat® RTM 50, Empigen® CSC, Swanol® Lanoquat DES-50, Rewoquat® UTM 50, Schercoquat® BAS, Lexquat® AMG-BEO, or Incroquat® Behenyl HE.

The aforementioned cationic surfactants can be used individually or in any combinations with one another, wherein they are included in amounts of between 0.01 and 10 wt. %, preferably in amounts from 0.01 to 7.5 wt. % and most particularly preferably in amounts from 0.1 to 5.0 wt. %. The very best results are obtained with amounts from 0.1 to 3.0 wt. %, relative in each case to the total composition of the individual agent.

Further quaternary ammonium compounds are cationic and amphoteric polymers.

The cationic and/or amphoteric polymers can be homopolymers or copolymers or polymers based on natural polymers, wherein the quaternary nitrogen groups can be included either in the polymer chain or preferably as a substituent on one or more of the monomers. The ammonium group-containing monomers can be copolymerized with non-cationic monomers. Suitable cationic monomers are unsaturated, radically polymerizable compounds bearing at least one cationic group, in particular ammonium-substituted vinyl monomers such as for example trialkyl methacryloxy alkylammonium, trialkyl acryloxy alkylammonium, dialkyl diallyl ammonium and quaternary vinyl ammonium monomers with cyclic groups that include cationic nitrogens, such as pyridinium, imidazolium or quaternary pyrrolidones, e.g. alkyl vinylimidazolium, alkyl vinylpyridinium, or alkyl vinylpyrrolidone salts. The alkyl groups of these monomers are preferably low alkyl groups such as for example C1 to C7 alkyl groups, particularly preferably C1 to C3 alkyl groups.

The ammonium group-containing monomers can be copolymerized with non-cationic monomers. Suitable comonomers are for example acrylamide, methacrylamide, alkyl and dialkyl acrylamide, alkyl and dialkyl methacrylamide, alkyl acrylate, alkyl methacrylate, vinyl caprolactone, vinylcaprolactam, vinylpyrrolidone, vinyl esters, for example vinyl acetate, vinyl alcohol, propylene glycol or ethylene glycol, the alkyl groups of these monomers preferably being C1 to C7 alkyl groups, particularly preferably C1 to C3 alkyl groups.

Among the large number of these polymers, the following have proved to be particularly effective constituents of the active agent complex according to the invention: Homopolymers of general formula —$\{CH_2—[CR^1COO—(CH_2)_mN^+R^2R^3R^4]\}_n$ $X^-$,
in which $R^1$=—H or —$CH_3$, $R^2$, $R^3$ and $R^4$ are selected independently of one another from C1-4 alkyl, alkenyl or hydroxyalkyl groups, m=1, 2, 3 or 4, n is a natural number and $X^-$ is a physiologically acceptable organic or inorganic anion. In the context of these polymers, those for which at least one of the following conditions applies are preferred according to the invention: $R^1$ denotes a methyl group, $R^2$, $R^3$ and $R^4$ denote methyl groups, m has the value 2.

Suitable physiologically acceptable counterions $X^-$ are for example halide ions, sulfate ions, phosphate ions, methosulfate ions as well as organic ions such as lactate, citrate, tartrate and acetate ions. Methosulfates and halide ions, in particular chloride, are preferred.

Suitable cationic polymers are for example copolymers according to the formula (Copo), which are preferably included in the hair treatment agents according to the invention in an amount—relative to their weight—from 0.001 to 5 wt. %, preferably 0.0025 to 2.5 wt. %, particularly preferably 0.005 to 1 wt. %, more preferably 0.0075 to 0.75 wt. % and in particular 0.01 to 0.5 wt. %.

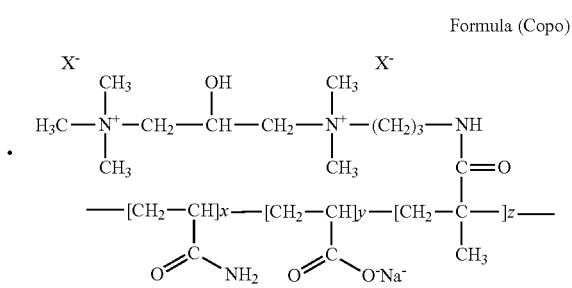

Formula (Copo)

in which:

$x+y+z=Q$

Q denotes values from 3 to 55,000, preferably from 10 to 25,000, particularly preferably from 50 to 15,000, more preferably from 100 to 10,000, still more preferably from 500 to 8000 and in particular from 1000 to 5000, x denotes (0 to 0.5) Q, preferably (0 to 0.3) Q and in particular the values 0, 1, 2, 3, 4, 5, the value 0 being preferred, y denotes (0.1 to 0.95) Q, preferably (0.5 to 0.7) Q and in particular values from 1 to 24,000, preferably from 5 to 15,000, particularly preferably from 10 to 10,000 and in particular from 100 to 4800, z denotes (0.001 to 0.5) Q, preferably (0.1 to 0.5) Q and in particular values from 1 to 12,500, preferably from 2 to 8000, particularly preferably from 3 to 4000 and in particular from 5 to 2000.

Irrespective of which of the preferred copolymers of formula (Copo) are used, hair treatment agents according to the invention are preferred which are characterized in that the ratio of (y:z) is 4:1 to 1:2, preferably 4:1 to 1:1.

Irrespective of which copolymers are used in the agents according to the invention, hair treatment agents according to the invention are preferred in which the copolymer has a molar mass from 10,000 to 20 million gmol$^{-1}$, preferably from 100,000 to 10 million gmol$^{-1}$, more preferably from 500,000 to 5 million gmol$^{-1}$ and in particular from 1.1 million to 2.2 million gmol$^{-1}$.

A most highly preferred copolymer, which is synthesized as described above, is commercially available under the name Polyquaternium-74.

A particularly suitable homopolymer is the optionally crosslinked poly(methacryloyloxyethyl trimethylammonium chloride) with the INCI name Polyquaternium-37. Such products are commercially available for example under the names Rheocare® CTH (Cosmetic Rheologies) and Synthalen® CR (3V Sigma).

The homopolymer is preferably used in the form of a non-aqueous polymer dispersion. Such polymer dispersions are commercially available under the names Salcare® SC 95 and Salcare® SC 96.

Suitable cationic polymers that are derived from natural polymers are cationic derivatives of polysaccharides, for example cationic derivatives of cellulose, starch or guar. Also suitable are chitosan and chitosan derivatives. Cationic polysaccharides have the general formula G-O—B—N$^+$ R$_a$R$_b$R$_c$ A$^-$ G is an anhydroglucose residue, for example starch or cellulose anhydroglucose;

B is a divalent group of compounds, for example alkylene, oxyalkylene, polyoxyalkylene or hydroxyalkylene;

R$_a$, R$_b$ and R$_c$ are independently of one another alkyl, aryl, alkylaryl, arylalkyl, alkoxyalkyl or alkoxyaryl, each having up to 18 C atoms, the total number of C atoms in R$_a$, R$_b$ and R$_c$ preferably being a maximum of 20;

A$^-$ is a conventional counteranion and is preferably chloride.

Cationic, i.e. quaternized, celluloses are available on the market with varying degrees of substitution, cationic charge density, nitrogen content and molecular weights. For example, Polyquaternium-67 is commercially available under the names Polymer® SL or Polymer® SK (Amerchol). A further most highly preferred cellulose is available from Croda under the trade name Mirustyle® CP. This is a trimonium and cocodimonium hydroxyethylcellulose as a derivatized cellulose with the INCI name Polyquaternium-72. Polyquaternium-72 can be used both in solid form and pre-dissolved in aqueous solution.

Further cationic celluloses are Polymer JR® 400 (Amerchol, INCI name Polyquaternium-10) and Polymer Quatrisoft® LM-200 (Amerchol, INCI name Polyquaternium-24). Further commercial products are the compounds Celquat® H 100 and Celquat® L 200. Particularly preferred cationic celluloses are Polyquaternium-24, Polyquaternium-67 and Polyquaternium-72.

Suitable cationic guar derivatives are sold under the trade name Jaguar® and have the INCI name Guar Hydroxypropyltrimonium Chloride. Particularly suitable cationic guar derivatives are also sold furthermore by Hercules under the name N-Hance®. Further cationic guar derivatives are sold by Cognis under the name Cosmedia®. A preferred cationic guar derivative is the commercial product AquaCat® from Hercules. This raw material is a pre-dissolved cationic guar derivative. The cationic guar derivatives are preferred according to the invention.

A suitable chitosan is sold for example by Kyowa Oil & Fat, Japan, under the trade name Flonac®. A preferred chitosan salt is chitosonium pyrrolidone carboxylate, which is sold for example under the name Kytamer® PC by Amerchol, USA. Further chitosan derivatives are freely available commercially under the trade names Hydagen® CMF, Hydagen® HCMF and Chitolam® NB/101.

A further group of extremely suitable polymers according to the invention are glucose-based polymers. The figure below shows such a cationic alkyl oligoglucoside.

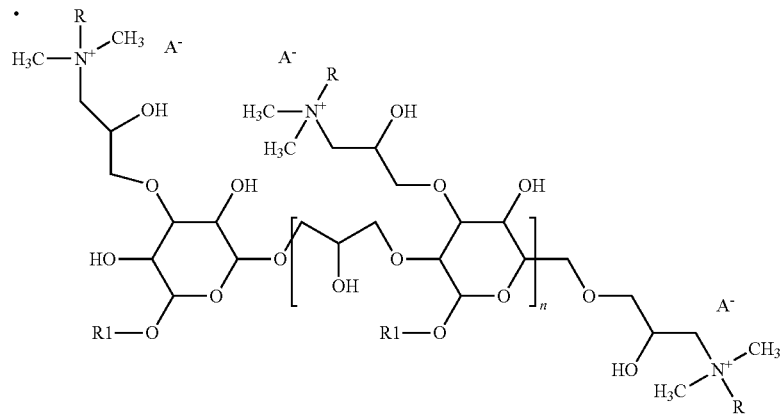

In the above formula the residues R independently of one another denote a linear or branched C6 to C30 alkyl residue, a linear or branched C6 to C30 alkenyl residue; the residue R preferably denotes a residue R selected from: lauryl, myristyl, cetyl, stearyl, oleyl, behenyl or arachidyl.

The residues R1 independently of one another denote a linear or branched C6 to C30 alkyl residue, a linear or branched C6 to C30 alkenyl residue; the residue R preferably denotes a residue selected from: butyl, capryl, caprylyl, octyl, nonyl, decanyl, lauryl, myristyl, cetyl, stearyl, oleyl, behenyl or arachidyl. The residues R1 are particularly preferably identical. Still more preferably, the residues R1 are selected from technical mixtures of the fatty alcohol cuts from C6/C8 fatty alcohols, C8/C10 fatty alcohols, C10/C12 fatty alcohols, C12/C14 fatty alcohols and C12/C18 fatty alcohols, and those technical fatty alcohol cuts which are of plant origin are most highly preferred. The counterion for cationic charging is a physiologically acceptable anion, for example halide, methosulfate, phosphate, citrate, tartrate, etc. The counterion is preferably a halide, such as fluoride, chloride, bromide or methosulfate. The anion is most highly preferably chloride.

Particularly preferred examples of the cationic alkyl oligoglucosides are the compounds with the INCI names Polyquaternium-77, Polyquaternium-78, Polyquaternium-79, Polyquaternium-80, Polyquaternium-81 and Polyquaternium-82. The cationic alkyl oligoglucosides with the names Polyquaternium-77, Polyquaternium-81 and Polyquaternium-82 are most highly preferred.

Such compounds can be obtained for example from Colonial Chemical Inc. under the name Poly Suga® Quat.

The cationic alkyl oligoglucosides are used in a total amount from 0.01 to 10.0 wt. %, preferably from 0.05 to 5.0 wt. %, more preferably from 0.1 to 3.0 wt. % and most highly preferably in amounts from 0.2 to 2.0 wt. %, relative in each case to the total weight of the composition. The fact that mixtures of cationic alkyl oligoglucosides can be used is also encompassed according to the invention of course. In this case it is preferable for a long-chain and a short-chain cationic alkyl oligoglucoside to be used at the same time in each case.

A further preferred cationic polymer can be obtained on the basis of ethanolamine. The polymer is commercially available under the name Polyquaternium-71.

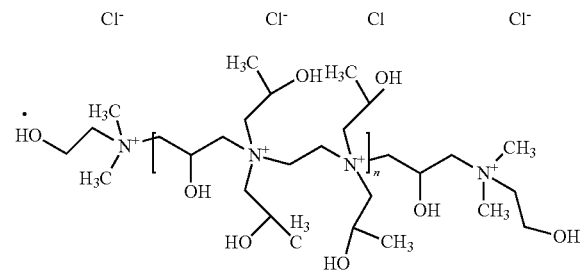

This polymer can be obtained for example from Colonial Chemical Inc. under the name Cola® Moist 300 P.

Polyquaternium-71 is used in a total amount from 0.01 to 10.0 wt. %, preferably from 0.05 to 5.0 wt. %, more preferably from 0.1 to 3.0 wt. % and most highly preferably in amounts from 0.2 to 2.0 wt. %, relative in each case to the total weight of the composition.

Furthermore a cationic alkyl oligoglucoside as shown in the figure below can be used to particular advantage.

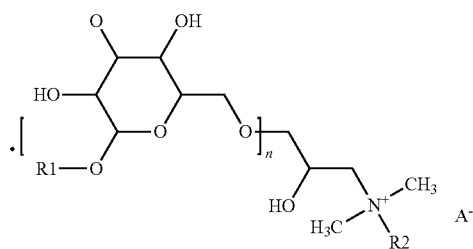

In the above formula the residue R2 denotes a linear or branched C6 to C30 alkyl residue, a linear or branched C6 to C30 alkenyl residue; the residue R preferably denotes a residue R selected from: lauryl, myristyl, cetyl, stearyl, oleyl, behenyl or arachidyl. The residue R1 denotes a linear or branched C6 to C30 alkyl residue, a linear or branched C6 to C30 alkenyl residue; the residue R1 preferably denotes a residue selected from: butyl, capryl, caprylyl, octyl, nonyl, decanyl, lauryl, myristyl, cetyl, stearyl, oleyl, behenyl or arachidyl. Still more preferably, the residue R1 is selected from technical mixtures of the fatty alcohol cuts from C6/C8 fatty alcohols, C8/C10 fatty alcohols, C10/C12 fatty alcohols, C12/C14 fatty alcohols and C12/C18 fatty alcohols, and those technical fatty alcohol cuts which are of plant origin are most highly preferred. The index n denotes a number between 1 and 20, preferably between 1 and 10, more preferably between 1 and 5 and most highly preferably between 1 and 3. The counterion for cationic charging, $A^-$, is a physiologically acceptable anion, for example halide, methosulfate, phosphate, citrate, tartrate, etc. The counterion is preferably a halide, such as fluoride, chloride, bromide or methosulfate. The anion is most highly preferably chloride.

Particularly preferred examples of the cationic alkyl oligoglucosides are the compounds with the INCI names Laurdimoniumhydroxypropyl Decylglucosides Chloride, Laurdimoniumhydroxypropyl Laurylglucosides Chloride, Stearyldimoniumhydroxypropyl Decylglucosides Chloride, Stearyldimoniumhydroxypropyl Laurylglucosides Chloride, Stearyldimoniumhydroxypropyl Laurylglucosides Chloride or Cocoglucosides Hydroxypropyltrimonium Chloride.

Such compounds can be obtained for example from Colonial Chemical Inc. under the name Suga® Quat.

The cationic alkyl oligoglucosides are used in a total amount from 0.01 to 10.0 wt. %, preferably from 0.05 to 5.0 wt. %, more preferably from 0.1 to 3.0 wt. % and most highly preferably in amounts from 0.2 to 2.0 wt. %, relative in each case to the total weight of the composition. The fact that mixtures of cationic alkyl oligoglucosides can be used is also encompassed according to the invention of course. In this case it is preferable for a long-chain and a short-chain cationic alkyl oligoglucoside to be used at the same time in each case.

A particularly preferred cationic polymer according to the invention is the copolymer of N-vinylpyrrolidone, N-vinylcaprolactam, N-(3-dimethylaminopropyl) methacrylamide and 3-(methacryloylamino)propyl lauryl dimethylammonium chloride (INCI name Polyquaternium-69), which is sold for example by ISP under the trade name AquaStyle® 300 (28-32 wt. % active substance in an ethanol-water blend, molecular weight 350,000).

Further preferred cationic polymers are for example
  cationized honey, for example the commercial product Honeyquat® 50,
  polymeric dimethyldiallyl ammonium salts and copolymers thereof with esters and amides of acrylic acid and methacrylic acid. The products available commercially under the names Merquat® 100 (poly(dimethyldiallyl ammonium chloride)) and Merquat® 550 (dimethyldiallyl ammonium chloride-acrylamide copolymer) are examples of such cationic polymers with the INCI name Polyquaternium-7, vinylpyrrolidone-vinylimidazolium methochloride copolymers, such as are sold under the names Luviquat® FC 370, FC 550 and the INCI name Polyquaternium-16 as well as FC 905 and HM 552, quaternized vinylpyrrolidone/dimethylaminoethyl methacrylate, for example vinylpyrrolidone/dimethylaminoethyl methacrylate methosulfate copolymer, which is sold under the trade names Gafquat® 755 N and Gafquat® 734 by Gaf Co., USA and the INCI name Polyquaternium-11, quaternized polyvinyl alcohol, and the polymers known under the names Polyquaternium-2, Polyquaternium-17, Polyquaternium-18 and Polyquaternium-27 with quaternary nitrogen atoms in the polymer main chain, vinylpyrrolidone-vinylcaprolactam-acrylate terpolymers, such as are available commercially with acrylic acid esters and acrylic acid amides as the third monomer unit under the name Aquaflex® SF 40, for example.

Amphoteric polymers according to the invention are polymers in which a cationic group is derived from at least one of the following monomers:

(i) monomers having quaternary ammonium groups of the general formula (Mono1), $$R^1\text{---CH}\!=\!\!CR^2\text{---CO---Z---}(C_nH_{2n})\text{---N}^{(+)}R^2R^3R^4 \quad A^{(-)} \quad \text{(Mono1)}$$

in which $R^1$ and $R^2$ independently of one another denote hydrogen or a methyl group and $R^3$, $R^4$ and $R^5$ independently of one another denote alkyl groups having 1 to 4 carbon atoms, Z is an NH group or an oxygen atom, n is an integer from 2 to 5 and $A^{(-)}$ is the anion of an organic or inorganic acid, (ii) monomers having quaternary ammonium groups of the general formula (Mono2),

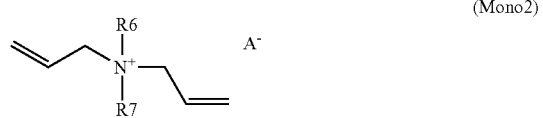

(Mono2)

in which $R^6$ and $R^7$ independently of one another denote a ($C_1$ to $C_4$) alkyl group, in particular a methyl group, and $A^-$ is the anion of an organic or inorganic acid, (iii) monomeric carboxylic acids of the general formula (Mono3), $$R^8\text{---CH}\!=\!\!CR^9\text{---COOH} \quad \text{(Mono3)}$$

in which $R^8$ and $R^9$ are independently of one another hydrogen or methyl groups.

Polymers in which monomers of type (i) are used, in which $R^3$, $R^4$ and $R^5$ are methyl groups, Z is an NH group and $A^{(-)}$ is a halide, methoxy sulfate or ethoxy sulfate ion, are particularly preferred; acrylamidopropyl trimethylammonium chloride is a particularly preferred monomer (i). Acrylic acid is preferably used as the monomer (ii) for the cited polymers.

Particularly preferred amphoteric polymers are copolymers of at least one monomer (Mono1) or (Mono2) with the monomer (Mono3), in particular copolymers of monomers (Mono2) and (Mono3). Amphoteric polymers that are most particularly preferably used according to the invention are copolymers of diallyldimethylammonium chloride and acrylic acid. These copolymers are sold under the INCI name Polyquaternium-22, inter alia under the trade name Merquat® 280 (Nalco).

In addition to a monomer (Mono1) or (Mono2) and a monomer (Mono3), the amphoteric polymers according to the invention can moreover additionally include a monomer (Mono4)

(iv) monomeric carboxylic acid amides of the general formula (Mono4),

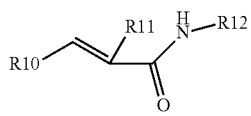

in which $R^{10}$ and $R^{11}$ are independently of one another hydrogen or methyl groups and $R^{12}$ denotes a hydrogen atom or a ($C_1$ to $C_8$) alkyl group.

Amphoteric polymers based on a comonomer (Mono4) that are most particularly preferably used according to the invention are terpolymers of diallyldimethylammonium chloride, acrylamide and acrylic acid. These copolymers are sold under the INCI name Polyquaternium-39, inter alia under the trade name Merquat® Plus 3330 (Nalco).

The amphoteric polymers can generally be used according to the invention both directly and in the form of the salt, which is obtained by neutralization of the polymers, with an alkali hydroxide for example.

The aforementioned cationic polymers can be used individually or in any combinations with one another, wherein they are included in amounts of between 0.01 and 10 wt. %, preferably in amounts from 0.01 to 7.5 wt. % and most particularly preferably in amounts from 0.1 to 5.0 wt. %. The very best results are obtained with amounts from 0.1 to 3.0 wt. %, relative in each case to the total composition of the individual agent.

In addition to the active agent combination according to the invention the hair treatment agents according to the invention naturally also include further constituents that are conventionally used in cosmetic compositions. The choice of these constituents is generally governed by the intended use of the hair treatment agents. In the case of a shampoo, for example, it includes further surface-active substances. In the case of hair masks, they optionally include further cationic compounds and further care substances.

In a particularly preferred embodiment of the active agent complex according to the invention the agents according to the invention preferably include at least one amino-functional silicone. Such silicones can be described for example by the formula (Si-2)

$$M(R_aQ_bSiO_{(4-a-b)/2})_x(R_cSiO_{(4-c)/2})_yM \quad \text{(Si-2)}$$

wherein in the above formula

R is a hydrocarbon or a hydrocarbon residue having 1 to approximately 6 carbon atoms, Q is a polar residue of the general formula —$R^1HZ$, in which $R^1$ is a divalent linking group that is bound to hydrogen and to the residue Z, composed of carbon and hydrogen atoms, carbon, hydrogen and oxygen atoms or carbon, hydrogen and nitrogen atoms, and Z is an organic, amino-functional residue that includes at least one amino-functional group;

a assumes values in the range from approximately 0 to approximately 2, b assumes values in the range from approximately 1 to approximately 3, a+b is less than or equal to 3, and c is a number in the range from approximately 1 to approximately 3, and x is a number in the range from 1 to approximately 2000, preferably from approximately 3 to approximately 50 and most preferably from approximately 3 to approximately 25, and y is a number in the range from approximately 20 to approximately 10,000, preferably from approximately 125 to approximately 10,000 and most preferably from approximately 150 to approximately 1000, and M is a suitable silicone end group as is known in the prior art, preferably trimethylsiloxy.

According to formula (Si-2) Z is an organic, amino-functional residue that includes at least one functional amino group. A possible formula for said Z is $NH(CH_2)_zNH_2$, in which z is an integer greater than or equal to 1. Another possible formula for said Z is $—NH(CH_2)_z(CH_2)_{zz}NH$, in which both z and zz are independently of one another an integer greater than or equal to 1, this structure encompassing diamino ring structures, such as piperazinyl. Said Z is most preferably an $—NHCH_2CH_2NH_2$ residue. Another possible formula for said Z is $—N(CH_2)_z(CH_2)_{zz}NX_2$ or $—NX_2$, in which each X of $X_2$ is selected independently from the group consisting of hydrogen and alkyl groups having 1 to 12 carbon atoms, and zz is 0.

Q according to formula (Si-2) is most preferably a polar amino-functional residue of the formula $—CH_2CH_2CH_2NHCH_2CH_2NH_2$.

In formula (Si-2) a assumes values in the range from 0 to 2, b assumes values in the range from 2 to 3, a+b is less than or equal to 3, and c is a number in the range from 1 to 3. Cationic silicone oils such as for example the commercially available products Dow Corning (DC) 929 Emulsion, DC 2-2078, DC 5-7113, SM-2059 (General Electric) and SLM-55067 (Wacker) are suitable according to the invention.

Particularly preferred agents according to the invention are characterized in that they include at least one amino-functional silicone of formula (Si-3a)

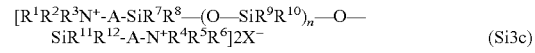

(Si-3a)

in which m and n are numbers whose sum (m+n) is between 1 and 2000, preferably between 50 and 150, wherein n preferably assumes values from 0 to 1999 and in particular from 49 to 149 and m preferably assumes values from 1 to 2000, in particular from 1 to 10.

Under the INCI declaration these silicones are known as trimethylsilylamodimethicones and they are available for example under the name Q2-7224 (manufacturer: Dow Corning; a stabilized trimethylsilylamodimethicone).

Also particularly preferred are agents according to the invention which include an amino-functional silicone of formula (Si-3b)

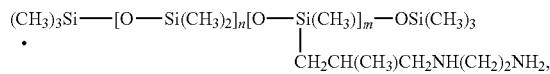

(Si-3b)

in which
R denotes —OH, an (optionally ethoxylated and/or propoxylated) ($C_1$ to $C_{20}$) alkoxy group or a —$CH_3$ group,
R' denotes —OH, a ($C_1$ to $C_{20}$) alkoxy group or a —$CH_3$ group, and
m, n1 and n2 are numbers whose sum (m+n1+n2) is between 1 and 2000, preferably between 50 and 150, wherein the sum (n1+n2) preferably assumes values from 0 to 1999 and in particular from 49 to 149 and m preferably assumes values from 1 to 2000, in particular from 1 to 10.

Under the INCI declaration these silicones are known as amodimethicones or as functionalized amodimethicones, such as for example Bis(C13-15 Alkoxy) PG Amodimethicone (available for example as the commercial product DC 8500 from Dow Corning).

Suitable diquaternary silicones are selected from compounds of general formula (Si3c)

$$[R^1R^2R^3N^+\text{-}A\text{-}SiR^7R^8\text{—}(O\text{—}SiR^9R^{10})_n\text{—}O\text{—}SiR^{11}R^{12}\text{-}A\text{-}N^+R^4R^5R^6]2X^-$$ (Si3c)

in which residues R1 to R6 independently of one another denote C1 to C22 alkyl residues, which can include hydroxyl groups, and wherein preferably at least one of the residues has at least 8 C atoms and the other residues have 1 to 4 C atoms, residues R7 to R12 independently of one another are the same or different and denote C1 to C10 alkyl or phenyl, A denotes a divalent organic group of compounds, n is a number from 0 to 200, preferably from 10 to 120, particularly preferably from 10 to 40, and $X^-$ is an anion.

The divalent group of compounds is preferably a C1 to C12 alkylene or alkoxyalkylene group, which can be substituted with one or more hydroxyl groups. The group $—(CH_2)_3—O—CH_2—CH(OH)—CH_2—$ is particularly preferred.

The anion $X^-$ can be a halide ion, an acetate, an organic carboxylate or a compound of the general formula $RSO_3^-$, in which R has the meaning of C1 to C4 alkyl residues.

A preferred diquaternary silicone has the general formula (Si3d)

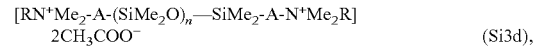

(Si3d), in which A is the group $—(CH_2)_3—O—CH_2—CH(OH)—CH_2—$,

R is an alkyl residue having at least 8 C atoms and n is a number from 10 to 120.

Suitable silicone polymers having two terminal, quaternary ammonium groups are known under the INCI name Quaternium-80. These are dimethyl siloxanes having two terminal trialkylammonium groups. Such diquaternary polydimethyl siloxanes are sold by Evonik under the trade names Abil® Quat 3270, 3272 and 3474.

Hair treatment agents that are preferred according to the invention are characterized in that they include, relative to their weight, 0.01 to 10 wt. %, preferably 0.01 to 8 wt. %, particularly preferably 0.1 to 7.5 wt. % and in particular 0.2 to 5 wt. % of amino-functional silicone(s) and/or diquaternary silicone.

Polyammonium-polysiloxane compounds represent a further silicone according to the invention having amino functions. The polyammonium-polysiloxane compounds can be purchased for example from GE Bayer Silicones under the trade name Baysilone®. The products with the names Baysilone TP 3911, SME 253 and SFE 839 are preferred here. The use of Baysilone TP 3911 as the active component of the compositions according to the invention is most particularly preferred. The polyammonium-polysiloxane compounds are used in the compositions according to the invention in an amount from 0.01 to 10 wt. %, preferably 0.01 to 7.5, particularly preferably 0.01 to 5.0 wt. %, most particularly preferably from 0.05 to 2.5 wt. %, relative in each case to the total composition.

EP 1887024 A1 describes novel cationic amino-functional silicones, which in particular improve the shine in agents for the care of surfaces, for example human hair. These cationic silicone polymers are characterized in that they have a silicone framework and at least one polyether part and moreover at least one part having an ammonium structure. Examples of the preferred cationic silicone polymers within the meaning of the present invention, in addition to the compounds of the aforementioned EP 1887024 A1, are moreover in particular the compounds having the INCI names: Silicone Quaternium-1, Silicone Quaternium-2, Silicone Quaternium-3, Silicone Quaternium-4, Silicone Quaternium-5, Silicone Quaternium-6, Silicone Quaternium-7, Silicone Quaternium-8, Silicone Quaternium-9, Silicone Quaternium-10, Silicone Quaternium-11, Silicone Quaternium-12, Silicone Quaternium-15, Silicone Quaternium-16, Silicone Quaternium-17, Silicone Quaternium-18, Silicone Quaternium-20, Silicone Quaternium-21, Silicone Quaternium-22 and Silicone Quaternium-2 Panthenol Succinate and Silicone Quaternium-16/Glycidyl Dimethicone Crosspolymer. Silicone Quaternium-22 is most preferred in particular. This raw material is sold for example by Evonik under the trade name Abil® T-Quat 60.

A last amino silicone that is particularly preferred according to the invention corresponds to the following formula:

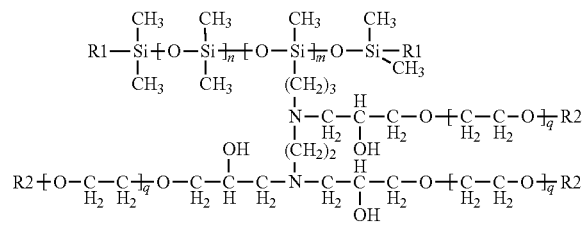

in which R1 denotes a methyl, ethyl, hydroxyl, methoxy or ethoxy group,

R2 denotes a straight-chain or branched C8 to C24 alkyl or alkylene residue, preferably a straight-chain or branched C9 to C22 alkyl or alkenyl residue, particularly preferably a straight-chain or branched C11 to C18 alkyl or alkenyl residue, most highly preferably a corresponding alkyl residue, n and m each denote integers from 1 to 1000 and q denotes in each case an integer from 2 to 50, preferably 4 to 30, particularly preferably 4 to 18 and most highly preferably from 4 to 12.

The molecular weight of such compounds is 15,000 to 2,000,000, measured with a Brookfield RV rotary viscometer, spindle 5, at 20° C. The molecular weight is preferably 30,000 to 1,750,000 and particularly preferably 50,000 to 1,500,000. The nitrogen content of the silicones according to the invention is 0.03 to 4.2 wt. %, preferably 0.1 to 2.8 wt. % and most highly preferably 0.16 to 1.4 wt. %. Amino-functional cationic silicones according to the invention of the above formula can be obtained from Clariant for example. A most highly preferred product according to the invention is commercially available under the INCI name Trideceth-9-Amodimethicone and Trideceth-12.

The cationic amino-functional silicone polymers of the above formula are included in the compositions according to the invention in amounts from 0.01 to 5 wt. %, preferably in amounts from 0.05 to 5 wt. % and most particularly preferably in amounts from 0.1 to 5 wt. %. The very best results are obtained with amounts from 0.1 to 2.5 wt. %, relative in each case to the total composition of the individual agent.

The cationic amino-functional silicone polymers are included in the compositions according to the invention in amounts from 0.01 to 10 wt. %, preferably in amounts from 0.05 to 10 wt. % and most particularly preferably in amounts from 0.1 to 7.5 wt. %. The very best results are obtained with amounts from 0.1 to 5 wt. %, relative in each case to the total composition of the individual agent.

The dimethicones according to the invention can be both linear and branched and also cyclic or cyclic and branched. Linear dimethicones can be represented by the following structural formula (Si1):

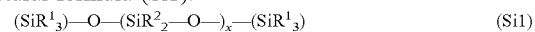

(Si1)

Branched dimethicones can be represented by the structural formula (Si1.1):

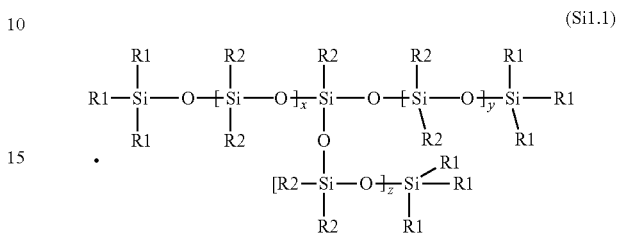

(Si1.1)

Residues $R^1$ and $R^2$ independently of one another denote hydrogen, a methyl residue, a C2 to C30 linear, saturated or unsaturated hydrocarbon residue, a phenyl residue and/or an aryl residue. The numbers x, y and z are integers and each run independently of one another from 0 to 50,000. The molecular weights of the dimethicones are between 1000 D and 10,000,000 D. The viscosities are between 100 and 10,000,000 cPs, measured at 25° C. with a glass capillary viscometer in accordance with the Dow Corning corporate test method CTM 0004 of 20 Jul. 1970. Preferred viscosities are between 1000 and 5,000,000 cPs, most particularly preferred viscosities are between 10,000 and 3,000,000 cPs. The most preferred range is between 50,000 and 2,000,000 cPs. Viscosities around the range of approximately 60,000 cPs are most highly preferred. Reference is made here by way of example to the product "Dow Corning 200 with 60,000 cSt".

Particularly preferred cosmetic or dermatological preparations according to the invention are characterized in that they include at least one silicone of formula (Si1.2)

$(CH_3)_3Si—[O—Si(CH_3)_2]_x—O—Si(CH_3)_3$ (Si1.2), in which x denotes a number from 0 to 100, preferably from 0 to 50, more preferably from 0 to 20 and in particular 0 to 10.

The dimethicones (Si1) are included in the compositions according to the invention in amounts from 0.01 to 10 wt. %, preferably 0.01 to 8 wt. %, particularly preferably 0.1 to 7.5 wt. % and in particular 0.1 to 5 wt. %, relative to the total composition.

Finally, the silicone compounds are understood to include dimethiconols (Si8). The dimethiconols according to the invention can be both linear and branched and also cyclic or cyclic and branched. Linear dimethiconols can be represented by the following structural formula (Si8-I):

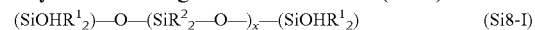

(Si8-I)

Branched dimethiconols can be represented by the structural formula (Si8-II):

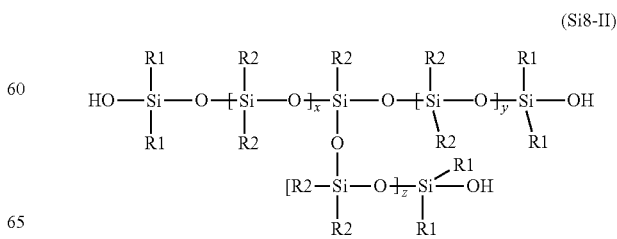

(Si8-II)

Residues $R^1$ and $R^2$ independently of one another denote hydrogen, a methyl residue, a C2 to C30 linear, saturated or unsaturated hydrocarbon residue, a phenyl residue and/or an aryl residue. The numbers x, y and z are integers and each run independently of one another from 0 to 50,000. The molecular weights of the dimethiconols are between 1000 D and 10,000,000 D. The viscosities are between 100 and 10,000,000 cPs, measured at 25° C. with a glass capillary viscometer in accordance with the Dow Corning corporate test method CTM 0004 of 20 Jul. 1970. Preferred viscosities are between 1000 and 5,000,000 cPs, most particularly preferred viscosities are between 10,000 and 3,000,000 cPs. The most preferred range is between 50,000 and 2,000,000 cPs.

The following commercial products are cited as examples of such products: Dow Corning 1-1254 Fluid, Dow Corning 2-9023 Fluid, Dow Corning 2-9026 Fluid, Abil OSW 5 (Degussa Care Specialties), Dow Corning 1401 Fluid, Dow Corning 1403 Fluid, Dow Corning 1501 Fluid, Dow Corning 1784 HVF Emulsion, Dow Corning 9546 Silicone Elastomer Blend, SM555, SM2725, SM2765, SM2785 (these last four all GE Silicones), Wacker-Belsil CM 1000, Wacker-Belsil CM 3092, Wacker-Belsil CM 5040, Wacker-Belsil DM 3096, Wacker-Belsil DM 3112 VP, Wacker-Belsil DM 8005 VP, Wacker-Chemie GmbH).

The dimethiconols (Si8) are included in the compositions according to the invention in amounts from 0.01 to 10 wt. %, preferably 0.01 to 8 wt. %, particularly preferably 0.1 to 7.5 wt. % and in particular 0.1 to 5 wt % of dimethiconol, relative to the composition.

The cyclic dimethicones referred to under INCI as cyclomethicones can also be used to advantage according to the invention. Cosmetic or dermatological preparations according to the invention are preferred that include at least one silicone of formula (Si-4),

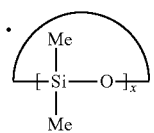
(Si-4)

in which x denotes a number from 3 to 200, preferably from 3 to 10, more preferably from 3 to 7 and in particular 3, 4, 5 or 6.

Agents that are likewise preferred according to the invention are characterized in that they include at least one silicone of formula (Si-5)

$$R_3Si\text{—}[O\text{—}SiR_2]_x\text{—}(CH_2)_n\text{—}[O\text{—}SiR_2]_y\text{—}O\text{—}SiR_3 \quad (Si\text{-}5)$$

in which R denotes identical or different residues from the group —H, -phenyl, -benzyl, —CH$_2$—CH(CH$_3$)Ph, C$_1$-C$_{20}$ alkyl residues, preferably —CH$_3$, —CH$_2$CH$_3$, —CH$_2$CH$_2$CH$_3$, —CH(CH$_3$)$_2$, —CH$_2$CH$_2$CH$_2$H$_3$, —CH$_2$CH(CH$_3$)$_2$, —CH(CH$_3$)CH$_2$CH$_3$, —C(CH$_3$)$_3$, x and y denote a number from 0 to 200, preferably from 0 to 10, more preferably from 0 to 7 and in particular 0, 1, 2, 3, 4, 5 or 6, and n denotes a number from 0 to 10, preferably from 1 to 8 and in particular 2, 3, 4, 5, 6.

As further silicones in addition to the dimethicones, dimethiconols, amodimethicones and/or cyclomethicones according to the invention, water-soluble silicones can be included in the compositions according to the invention.

Corresponding hydrophilic silicones are selected for example from the compounds of formulae (Si-6) and/or (Si-7). Silicone-based water-soluble surfactants which are preferred in particular are selected from the group of dimethicone copolyols, which are preferably alkoxylated, in particular polyethoxylated or polypropoxylated.

According to the invention dimethicone copolyols are understood to be preferably polyoxyalkylene-modified dimethyl polysiloxanes of the general formulae (Si-6) or (Si-7):

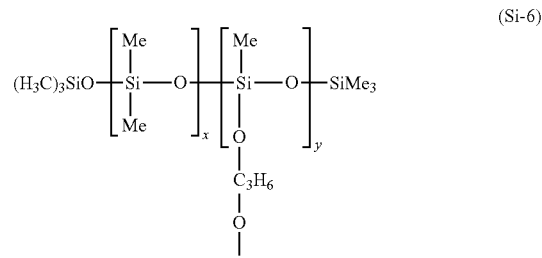
(Si-6)

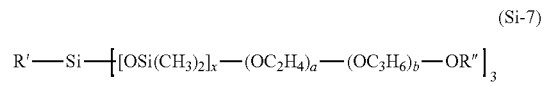
(Si-7)

in which the residue R denotes a hydrogen atom, an alkyl group having 1 to 12 C atoms, an alkoxy group having 1 to 12 C atoms or a hydroxyl group, the residues R' and R" denote alkyl groups having 1 to 12 C atoms, x denotes an integer from 1 to 100, preferably from 20 to 30, y denotes an integer from 1 to 20, preferably from 2 to 10, and a and b denote integers from 0 to 50, preferably 10 to 30.

Particularly preferred dimethicone copolyols within the meaning of the invention are for example the products sold commercially under the trade name SILWET (Union Carbide Corporation) and DOW CORNING. Dimethicone copolyols that are particularly preferred according to the invention are Dow Corning 190 and Dow Corning 193.

The dimethicone copolyols are included in the compositions according to the invention in amounts from 0.01 to 10 wt. %, preferably 0.01 to 8 wt. %, particularly preferably 0.1 to 7.5 wt. % and in particular 0.1 to 5 wt. % of dimethicone copolyol, relative to the composition.

Even though all silicones can be used with the active agent combination according to the invention, it has been found that the effect diminishes in the order amino-functional silicones, dimethicones comparable with dimethiconols, cyclomethicones and water-soluble silicones. If more than two silicones are used, combinations of amino-functional silicones with dimethicones and/or dimethiconols have proved to be most effective in increasing the effect of the active agent combination according to the invention. The very best effects are obtained if the silicone compounds already described as being particularly preferred are used as silicones.

A further preferred ingredient of the compositions according to the invention is a hydroxycarboxylic acid. Hydroxycarboxylic acids are carboxylic acids having both at least one carboxyl group and at least one hydroxyl group in the molecule. In particular, hydroxycarboxylic acids include the so-called AHA acids and β-hydroxycarboxylic acids. Another name for such hydroxy acids is fruit acid, because the acids frequently occur in fruits. The hydroxycarboxylic acid according to the invention is selected in particular from glycolic acid, lactic acid, glyceric acid, malic acid, citric acid, isocitric acid, mandelic acid, tartronic acid, tartaric acid, vanillic acid, salicylic acid, mevalonic acid, β-hydroxybutyric acid, gallic acid or protocatechuic acid. The hydroxycarboxylic acid is particularly preferably selected from glycolic acid, lactic acid, glyceric acid, malic acid, citric acid, mandelic acid, tartaric acid, vanillic acid and salicylic acid. The hydroxycarboxylic acid is most particularly preferably selected from glycolic acid, lactic acid, malic acid, citric acid, mandelic acid, tartaric acid and vanillic acid. The hydroxycarboxylic acid is most highly preferably selected from malic acid, mandelic acid, tartaric acid and vanillic acid. Mixtures of hydroxycarboxylic acids can of course also be used.

The compositions according to the invention include the hydroxycarboxylic acids in total in an amount from 0.01 to 15.0 wt. %, in particular from 0.01 to 10.0 wt. %, preferably from 0.1 to 7.5 wt. % and most highly preferably in an amount from 0.1 to 5.0 wt. %, relative in each case to the total composition.

A further ingredient which increases the effect of the active agent combination according to the invention is an oil body. These are to particular advantage ester oils, for example. Ester oils are defined as follows:

Ester oils are understood to be the esters of $C_6$-$C_{30}$ fatty acids with $C_2$-$C_{30}$ fatty alcohols. The monoesters of fatty acids with alcohols having 2 to 24 C atoms are preferred. Examples of fatty acid components used in the esters are hexanoic acid, octanoic acid, 2-ethylhexanoic acid, decanoic acid, lauric acid, isotridecanoic acid, myristic acid, palmitic acid, palmitoleic acid, stearic acid, isostearic acid, oleic acid, elaidic acid, petroselic acid, linoleic acid, linolenic acid, elaeostearic acid, eicosanoic acid, gadoleic acid, docosanoic acid and erucic acid and technical mixtures thereof. Examples of the fatty alcohol components in the ester oils are isopropyl alcohol, caproic alcohol, caprylic alcohol, 2-ethylhexyl alcohol, capric alcohol, lauryl alcohol, isotridecyl alcohol, myristyl alcohol, cetyl alcohol, palmoleyl alcohol, stearyl alcohol, isostearyl alcohol, oleyl alcohol, elaidyl alcohol, petroselinyl alcohol, linolyl alcohol, linolenyl alcohol, elaeostearyl alcohol, arachyl alcohol, gadoleyl alcohol, behenyl alcohol, erucyl alcohol and brassidyl alcohol and technical mixtures thereof. Particularly preferred according to the invention are isopropyl myristate (Rilanit® IPM), isononanoic acid C16-18 alkyl ester (Cetiol® SN), 2-ethylhexyl palmitate (Cegesoft® 24), stearic acid 2-ethylhexyl ester (Cetiol® 868), cetyl oleate, glycerol tricaprylate, coconut fatty alcohol caprinate/caprylate (Cetiol® LC), n-butyl stearate, oleyl erucate (Cetiol® J 600), isopropyl palmitate (Rilanit® IPP), oleyl oleate (Cetiol®), lauric acid hexyl ester (Cetiol® A), di-n-butyl adipate (Cetiol® B), myristyl myristate (Cetiol® MM), cetearyl isononanoate (Cetiol® SN), oleic acid decyl ester (Cetiol® V).

The ester oils can of course also be alkoxylated with ethylene oxide, propylene oxide or mixtures of ethylene oxide and propylene oxide. The alkoxylation can take place both on the fatty alcohol part and on the fatty acid part and also on both parts of the ester oils. It is preferred according to the invention, however, for the fatty alcohol to be alkoxylated first and then esterified with fatty acid. These compounds are shown in general in formula (D4-II).

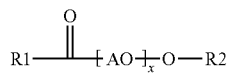

(D4-II)

R1 here denotes a saturated or unsaturated, branched or unbranched, cyclic saturated, cyclic unsaturated acyl residue having 6 to 30 carbon atoms,
AO denotes ethylene oxide, propylene oxide or butylene oxide,
X denotes a number between 1 and 200, preferably between 1 and 100, particularly preferably between 1 and 50, most particularly preferably between 1 and 20, most highly preferably between 1 and 10 and most preferably between 1 and 5, R2 denotes a saturated or unsaturated, branched or unbranched, cyclic saturated, cyclic unsaturated alkyl, alkenyl, alkynyl, phenyl or benzyl residue having 6 to 30 carbon atoms. Examples of fatty acid components used as residue R1 in the esters are hexanoic acid, octanoic acid, 2-ethylhexanoic acid, decanoic acid, lauric acid, isotridecanoic acid, myristic acid, palmitic acid, palmitoleic acid, stearic acid, isostearic acid, oleic acid, elaidic acid, petroselic acid, linoleic acid, linolenic acid, elaeostearic acid, eicosanoic acid, gadoleic acid, docosanoic acid and erucic acid and technical mixtures thereof. Examples of the fatty alcohol components as residue R2 in the ester oils are benzyl alcohol, isopropyl alcohol, caproic alcohol, caprylic alcohol, 2-ethylhexyl alcohol, capric alcohol, lauryl alcohol, isotridecyl alcohol, myristyl alcohol, cetyl alcohol, palmoleyl alcohol, stearyl alcohol, isostearyl alcohol, oleyl alcohol, elaidyl alcohol, petroselinyl alcohol, linolyl alcohol, linolenyl alcohol, elaeostearyl alcohol, arachyl alcohol, gadoleyl alcohol, behenyl alcohol, erucyl alcohol and brassidyl alcohol and technical mixtures thereof. An ester oil that is particularly preferred according to the invention is available for example under the INCI name PPG-3 Benzyl Ether Myristate.

Ester oils are also understood to include:
dicarboxylic acid esters such as di-n-butyl adipate, di-(2-ethylhexyl) adipate, di-(2-ethylhexyl) succinate and diisotridecyl acelate and also diol esters such as ethylene glycol dioleate, ethylene glycol diisotridecanoate, propylene glycol di-(2-ethyl hexanoate), propylene glycol diisostearate, propylene glycol dipelargonate, butanediol diisostearate, neopentyl glycol dicaprylate, and
symmetrical, asymmetrical or cyclic esters of carbonic acid with fatty alcohols, for example glycerol carbonate or dicaprylyl carbonate (Cetiol® CC),
tri-fatty acid esters of saturated and/or unsaturated linear and/or branched fatty acids with glycerol,
fatty acid partial glycerides, namely monoglycerides, diglycerides and technical mixtures thereof. Typical examples are mono- and/or diglycerides based on hexanoic acid, octanoic acid, 2-ethylhexanoic acid, decanoic acid, lauric acid, isotridecanoic acid, myristic acid, palmitic acid, palmoleic acid, stearic acid, isostearic acid, oleic acid, elaidic acid, petroselic acid, linoleic acid, linolenic acid, elaeostearic acid, eicosanoic acid, gadoleic acid, docosanoic acid and erucic acid and technical mixtures thereof. Oleic acid monoglycerides are preferably used.

The ester oils are used in the agents according to the invention in an amount from 0.01 to 20 wt. %, preferably 0.01 to 10.0 wt. %, particularly preferably 0.01 to 7.5 wt. %, most highly preferably from 0.1 to 5.0 wt. %. Naturally it is also possible according to the invention to use a plurality of ester oils at the same time.

Further oil bodies according to the invention are:
vegetable oils. Examples of such oils are sunflower oil, olive oil, soybean oil, rapeseed oil, almond oil, jojoba oil, orange oil, wheat germ oil, peach kernel oil and the liquid components of coconut oil. Other triglyceride oils are also suitable, however, such as the liquid components of beef fat and synthetic triglyceride oils.
liquid paraffin oils, isoparaffin oils and synthetic hydrocarbons and also di-n-alkyl ethers having in total between 12 and 36 C atoms, in particular between 12 and 24 C atoms, such as for example di-n-octyl ether, di-n-decyl ether, di-n-nonyl ether, di-n-undecyl ether, di-n-dodecyl ether, n-hexyl-n-octyl ether, n-oetyl-n-decyl ether, n-decyl-n-undecyl ether, n-undecyl-n-dodecyl ether and n-hexyl-n-undecyl ether and also di-tert-butyl ether, diisopentyl ether, di-3-ethyl decyl ether, tert-butyl-n-octyl ether, isopentyl-n-octyl ether and 2-methyl pentyl-n-octyl ether. The compounds available as commercial products, 1,3-di-(2-ethylhexyl) cyclohexane (Cetiol® S) and di-n-octyl ether (Cetiol® OE), can be preferred.

Amaranth seed oil, apricot kernel oil, argan oil, avocado oil, babassu oil, cottonseed oil, borage seed oil, camelina oil, thistle oil, groundnut oil, pomegranate kernel oil, grapefruit seed oil, hemp oil, hazelnut oil, elderberry seed oil, blackcurrant seed oil, jojoba oil, cocoa butter, linseed oil, macadamia nut oil, corn oil, almond oil, marula oil, evening primrose oil, olive oil, palm oil, rapeseed oil, rice oil, sea buckthorn fruit oil, sea buckthorn seed oil, sesame oil, shea butter, soybean oil, sunflower oil, grape seed oil, walnut oil or wild rose oil, for example, are used as natural oils.

In many cases the agents include at least one surface-active substance, with both anionic and zwitterionic, ampholytic, non-ionic and cationic surface-active substances being suitable in principle. The choice of surface-active substances is governed by the type of agent.

All anionic surface-active substances that are suitable for use on the human body are suitable as anionic surfactants (Tanion) in preparations according to the invention. Typical examples of anionic surfactants are:

linear and branched fatty acids having 8 to 30 C atoms (soaps),
ether carboxylic acids of the formula R—O—($CH_2$—$CH_2O$)$_x$—$CH_2$—COOH, in which R is a linear alkyl group having 8 to 30 C atoms and x=0 or 1 to 16, and salts thereof,
acyl sarcosides having 8 to 24 C atoms in the acyl group,
acyl taurides having 8 to 24 C atoms in the acyl group,
acyl isethionates having 8 to 24 C atoms in the acyl group,
sulfosuccinic acid mono- and dialkyl esters having 8 to 24 C atoms in the alkyl group and sulfosuccinic acid monoalkyl polyoxyethyl esters having 8 to 24 C atoms in the alkyl group and 1 to 6 oxyethyl groups,
linear alkane sulfonates having 8 to 24 C atoms,
linear alpha-olefin sulfonates having 8 to 24 C atoms,
alpha-sulfo fatty acid methyl esters of fatty acids having 8 to 30 C atoms,
alkyl sulfates and alkyl polyglycol ether sulfates of the formula R—O($CH_2$—$CH_2O$)$_x$—$OSO_3H$, in which R is a preferably linear alkyl group having 8 to 30 C atoms and x=0 or 1 to 12,
hydroxyl sulfonates substantially corresponding to at least one of the following two formulae or to mixtures and salts thereof, $CH_3$—($CH_2$)$_y$—CHOH—($CH_2$)$_p$—(CH—$SO_3M$)-($CH_2$)$_z$—$CH_2$—O—($C_nH_{2n}O$)$_x$—H, and/or $CH_3$—($CH_2$)$_y$—(CH—$SO_3M$)-($CH_2$)$_p$—CHOH—($CH_2$)$_z$—$CH_2$—O—($C_nH_{2n}O$)$_x$—H wherein in both formulae y and z=0 or integers from 1 to 18, p=0, 1 or 2 and the sum (y+z+p) is a number from 12 to 18, x=0 or a number from 1 to 30 and n is an integer from 2 to 4 and M=H or an alkali ion, in particular sodium, potassium, lithium, alkaline-earth ion, in particular magnesium, calcium, zinc and/or an ammonium ion, which can optionally be substituted, in particular mono-, di-, tri- or tetraammonium ions with C1 to C4 alkyl, alkenyl or aryl residues,
sulfated hydroxyalkyl polyethylene and/or hydroxyalkylene propylene glycol ethers of the formula $R^1$—(CHOS$O_3$M)-CH$R^3$—(OCH$R^4$—$CH_2$)$_n$—$OR^2$ in which $R^1$ denotes a linear alkyl residue having 1 to 24 C atoms, $R^2$ denotes a linear or branched, saturated alkyl residue having 1 to 24 C atoms, $R^3$ denotes hydrogen or a linear alkyl residue having 1 to 24 C atoms, $R^4$ denotes hydrogen or a methyl residue and M denotes hydrogen, ammonium, alkyl ammonium, alkanol ammonium, wherein the alkyl and alkanol residues each have 1 to 4 C atoms, or a metal atom selected from lithium, sodium, potassium, calcium or magnesium, and n denotes a number in the range from 0 to 12 and furthermore the total number of C atoms included in $R^1$ and $R^3$ is 2 to 44,
sulfonates of unsaturated fatty acids having 8 to 24 C atoms and 1 to 6 double bonds,
esters of tartaric acid and citric acid with alcohols which are addition products of approximately 2 to 15 molecules of ethylene oxide and/or propylene oxide with fatty alcohols having 8 to 22 C atoms,
alkyl and/or alkenyl ether phosphates of the formula

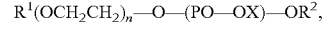

$R^1$(OCH$_2$CH$_2$)$_n$—O—(PO—OX)—$OR^2$, in which $R^1$ preferably denotes an aliphatic hydrocarbon residue having 8 to 30 carbon atoms, $R^2$ denotes hydrogen, a (CH$_2$CH$_2$O)$_n$$R^2$ residue or X, n denotes numbers from 1 to 10 and X denotes hydrogen, an alkali or alkaline-earth metal or N$R^3$$R^4$$R^5$$R^6$, with $R^3$ to $R^6$ independently of one another denoting hydrogen or a $C_1$ to $C_4$ hydrocarbon residue,
sulfated fatty acid alkylene glycol esters of the formula RCO(AlkO)$_n$SO$_3$M in which RCO— denotes a linear or branched, aliphatic, saturated and/or unsaturated acyl residue having 6 to 22 C atoms, Alk denotes CH$_2$CH$_2$, CHCH$_3$CH$_2$ and/or CH$_2$CHCH$_3$, n denotes numbers from 0.5 to 5 and M denotes a metal, such as alkali metal, in particular sodium, potassium, lithium, alkaline-earth metal, in particular magnesium, calcium, zinc, or ammonium ion, such as $^+$N$R^3$$R^4$$R^5$$R^6$, with $R^3$ to $R^6$ independently of one another denoting hydrogen or a $C_1$ to $C_4$ hydrocarbon residue,
monoglyceride sulfates and monoglyceride ether sulfates of the formula

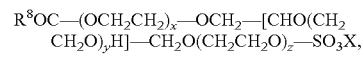

$R^8$OC—(OCH$_2$CH$_2$)$_x$—OCH$_2$—[CHO(CH$_2$CH$_2$O)$_y$H]—CH$_2$O(CH$_2$CH$_2$O)$_z$—SO$_3$X, in which $R^8$CO denotes a linear or branched acyl residue having 6 to 22 carbon atoms, x, y and z in total denote 0 or numbers from 1 to 30, preferably 2 to 10, and X denotes an alkali or alkaline-earth metal. Typical examples of suitable monoglyceride (ether) sulfates within the meaning of the invention are the reaction products of lauric acid monoglyceride, coconut fatty acid monoglyceride, palmitic acid monoglyceride, stearic acid monoglyceride, oleic acid monoglyceride and tallow fatty acid monoglyceride as well as the ethylene oxide adducts thereof with sulfur trioxide or chlorosulfonic acid in the form of their sodium salts. Monoglyceride sulfates are preferably used in which $R^8$CO denotes a linear acyl residue having 8 to 18 carbon atoms,
amide ether carboxylic acids, $R^1$—CO—N$R^2$—CH$_2$CH$_2$—O—(CH$_2$CH$_2$O)$_n$CH$_2$COOM, with $R^1$ as a straight-chain or branched alkyl or alkenyl residue having a number of carbon atoms in the chain from 2 to 30, n denotes an integer from 1 to 20 and $R^2$ denotes hydrogen, a methyl, ethyl, propyl, isopropyl, n-butyl, t-butyl or isobutyl residue and M denotes hydrogen or a metal such as alkali metal, in particular sodium, potassium, lithium, alkaline-earth metal, in particular magnesium, calcium, zinc, or an ammonium ion, such as $^+$N$R^3$$R^4$$R^5$$R^6$, with $R^3$ to $R^6$ independently of one another denoting hydrogen or a C1 to C4 hydrocarbon residue. Such products are available for example from Chem-Y under the product name Akypo®,
acyl glutamates of the formula XOOC—CH$_2$CH$_2$CH(C(NH)OR)—COOX, in which RCO denotes a linear or branched acyl residue having 6 to 22 carbon atoms and 0 and/or 1, 2 or 3 double bonds and X denotes hydrogen, an alkali and/or alkaline-earth metal, ammonium, alkyl ammonium, alkanol ammonium or glucammonium, condensation products of a water-soluble salt of a water-soluble protein hydrolysate with a C8-C30 fatty acid. Such products have long been available commercially under the trademark Lamepon®, Maypon®, Gluadin®, Hostapon® KCG or Amisoft®, alkyl and/or alkenyl oligoglycoside carboxylates, sulfates, phosphates and/or isethionates, acyl lactylates and hydroxy mixed ether sulfates.

If the gentle anionic surfactants include polyglycol ether chains, it is most particularly preferable for them to have a narrow homolog distribution. In the case of gentle anionic surfactants having polygycol ether units, it is furthermore preferable for the number of glycol ether groups to be 1 to 20, preferably 2 to 15, particularly preferably 2 to 12. Particularly gentle anionic surfactants having polyglycol ether groups without a narrow homolog distribution can also be obtained for example if the number of polyglycol ether groups is 4 to 12 and Zn or Mg ions are chosen as the counterion. One example is the commercial product Texapon® ASV.

Particularly suitable zwitterionic surfactants are the betaines such as N-alkyl-N,N-dimethylammonium glycinates, for example cocoalkyl dimethylammonium glycinate, N-acyl aminopropyl-N,N-dimethylammonium glycinates, for example cocoacylaminopropyl dimethylammonium glycinate, and 2-alkyl-3-carboxymethyl-3-hydroxyethyl imidazolines each having 8 to 18 C atoms in the alkyl or acyl group, and cocoacylaminoethyl hydroxyethyl carboxymethyl glycinate. A preferred zwitterionic surfactant is the fatty acid amide derivative known under the INCI name Cocamidopropyl Betaine.

Ampholytic surfactants (Tampho) are understood to be surface-active compounds that are capable of forming internal salts. Examples of suitable ampholytic surfactants are N-alkyl glycines, N-alkyl propionic acids, N-alkyl aminobutyric acids, N-alkyl iminodipropionic acids, N-hydroxyethyl-N-alkyl amidopropyl glycines, N-alkyl taurines, N-alkyl sarcosines, 2-alkyl aminopropionic acids and alkyl aminoacetic acids, each having approximately 8 to 24 C atoms in the alkyl group. Typical examples of amphoteric or zwitterionic surfactants are alkyl betaines, alkyl amido betaines, aminopropionates, aminoglycinates, imidazolinium betaines and sulfobetaines.

Particularly preferred ampholytic surfactants are N-cocoalkyl aminopropionate, cocoacylaminoethyl aminopropionate and $C_{12}$-$C_{18}$ acyl sarcosine.

Non-ionic surfactants (Tnio) are for example addition products of 2 to 50 mol of ethylene oxide and/or 0 to 5 mol of propylene oxide with linear and branched fatty alcohols having 6 to 30 C atoms, fatty alcohol polyglycol ethers or fatty alcohol polypropylene glycol ethers or mixed fatty alcohol polyethers, addition products of 2 to 50 mol of ethylene oxide and/or 0 to 5 mol of propylene oxide with linear and branched fatty acids having 6 to 30 C atoms, fatty acid polyglycol ethers or fatty acid polypropylene glycol ethers or mixed fatty acid polyethers, addition products of 2 to 50 mol of ethylene oxide and/or 0 to 5 mol of propylene oxide with linear and branched alkylphenols having 8 to 15 C atoms in the alkyl group, alkylphenol polyglycol ethers or alkyl polypropylene glycol ethers or mixed alkylphenol polyethers, addition products of 2 to 50 mol of ethylene oxide and/or 0 to 5 mol of propylene oxide with linear and branched fatty alcohols having 8 to 30 C atoms, with fatty acids having 8 to 30 C atoms and with alkylphenols having 8 to 15 C atoms in the alkyl group, end-capped with a methyl or $C_2$ to $C_6$ alkyl residue, such as for example the types available under the commercial names Dehydol® LS, Dehydol® LT (Cognis), $C_{12}$-$C_{30}$ fatty acid monoesters and diesters of addition products of 1 to 30 mol of ethylene oxide with glycerol, addition products of 5 to 60 mol of ethylene oxide with castor oil and hydrogenated castor oil, polyol fatty acid esters, such as for example the commercial product Hydagen® HSP (Cognis) or Sovermol® types (Cognis), alkoxylated triglycerides, alkoxylated fatty acid alkyl esters of formula (Tnio-1)

$$R^1CO\text{—}(OCH_2CHR^2)_wOR^3 \quad \text{(Tnio-1)}$$

in which $R^1CO$ denotes a linear or branched, saturated and/or unsaturated acyl residue having 6 to 22 carbon atoms, $R^2$ denotes hydrogen or methyl, $R^3$ denotes linear or branched alkyl residues having 1 to 4 carbon atoms and w denotes numbers from 1 to 20, amine oxides, hydroxy mixed ethers, $R^1O[CH_2CH(CH_3)O]_x(CH_2CHR^2O)_y[CH_2CH(OH)R^3]_z$ with $R^1$ denoting a linear or branched, saturated or unsaturated alkyl and/or alkenyl residue having 2 to 30 C atoms, $R^2$ denoting hydrogen, a methyl, ethyl, propyl or isopropyl residue, $R^3$ denoting a linear or branched alkyl residue having 2 to 30 C atoms, x denoting 0 or a number from 1 to 20, Y a number from 1 to 30 and z denoting the number 1, 2, 3, 4 or 5, sorbitan fatty acid esters and addition products of ethylene oxide with sorbitan fatty acid esters such as for example polysorbates, sugar fatty acid esters and addition products of ethylene oxide with sugar fatty acid esters, addition products of ethylene oxide with fatty acid alkanol amides and fatty amines, sugar surfactants of the alkyl and alkenyl oligoglycoside type, sugar surfactants of the fatty acid N-alkyl polyhydroxyalkylamide type, fatty acid amide polyglycol ethers, fatty amine polyglycol ethers, mixed ethers or mixed formals and polysorbates.

The surfactants (T) are used in amounts from 0.05 to 45 wt. %, preferably 0.1 to 30 wt. % and most particularly preferably from 0.5 to 25 wt. %, relative to the total agent used according to the invention.

Emulsifiers that can be used according to the invention are for example addition products of 4 to 30 mol of ethylene oxide and/or 0 to 5 mol of propylene oxide with linear fatty alcohols having 8 to 22 C atoms, with fatty acids having 12 to 22 C atoms and with alkylphenols having 8 to 15 C atoms in the alkyl group, $C_{12}$-$C_{22}$ fatty acid monoesters and diesters of addition products of 1 to 30 mol of ethylene oxide with polyols having 3 to 6 carbon atoms, in particular with glycerol, ethylene oxide and polyglycerol addition products with methyl glucoside fatty acid esters, fatty acid alkanol amides and fatty acid glucamides, $C_8$-$C_{22}$ alkyl mono- and oligoglycosides and ethoxylated analogs thereof, wherein degrees of oligomerization of 1.1 to 5, in particular 1.2 to 2.0, and glucose as the sugar component are preferred, mixtures of alkyl (oligo)glucosides and fatty alcohols, for example the commercially available product Montanov® 68, addition products of 5 to 60 mol of ethylene oxide with castor oil and hydrogenated castor oil, partial esters of polyols having 3 to 6 carbon atoms with saturated fatty acids having 8 to 22 C atoms, sterols, from both animal tissue (zoosterols, cholesterol, lanosterol) and vegetable fats (phytosterols, ergosterol, stigmasterol, sitosterol) or from fungi and yeasts (mycosterols), phospholipids (lecithins, phosphatidylcholines),
fatty acid esters of sugars and sugar alcohols, such as sorbitol,
polyglycerols and polyglycerol derivatives such as for example polyglycerol poly-12-hydroxystearate (commercial product Dehymuls® PGPH).

The agents according to the invention include the emulsifiers preferably in amounts from 0.1 to 25 wt. %, in particular 0.5 to 15 wt. %, relative to the total agent.

As a further active agent the compositions according to the invention include fats (Fat) to particular advantage. Fats (Fat) are understood to be fatty acids, fatty alcohols, natural and synthetic waxes, which can be present both in solid form and in liquid form in aqueous dispersion, and natural and synthetic cosmetic oil components.

Linear and/or branched, saturated and/or unsaturated fatty acids having 6 to 30 carbon atoms can be used as fatty acids (Fatac). Fatty acids having 10 to 22 carbon atoms are preferred. Examples which can be cited include the isostearic acids, such as the commercial products Emersol® 871 and Emersol® 875, and isopalmitic acids such as the commercial product Edenor® IP 95, as well as all further fatty acids sold under the Edenor® trade names (Cognis). Further typical examples of such fatty acids are hexanoic acid, octanoic acid, 2-ethylhexanoic acid, decanoic acid, lauric acid, isotridecanoic acid, myristic acid, palmitic acid, palmitoleic acid, stearic acid, isostearic acid, oleic acid, elaidic acid, petroselic acid, linoleic acid, linolenic acid, elaeostearic acid, eicosanoic acid, gadoleic acid, docosanoic acid and erucic acid and technical mixtures thereof. The fatty acid cuts obtainable from coconut oil or palm oil are conventionally particularly preferred; as a rule the use of stearic acid is preferred in particular.

The amount used here is 0.1 to 15 wt. %, relative to the total agent. The amount is preferably 0.5 to 10 wt. %, wherein amounts of 1 to 5 wt. % can be most particularly advantageous.

Saturated, mono- or polyunsaturated, branched or unbranched fatty alcohols having $C_6$ to $C_{30}$, preferably $C_{10}$ to $C_{22}$ and most particularly preferably $C_{12}$ to $C_{22}$ carbon atoms can be used as fatty alcohols (Fatal). Suitable for use within the meaning of the invention are for example decanol, octanol, octenol, dodecenol, decenol, octadienol, dodecadienol, decadienol, oleyl alcohol, erucic alcohol, ricinol alcohol, stearyl alcohol, isostearyl alcohol, cetyl alcohol, lauryl alcohol, myristyl alcohol, arachidyl alcohol, capryl alcohol, capric alcohol, linoleyl alcohol, linolenyl alcohol and behenyl alcohol, as well as the Guerbet alcohols thereof, wherein this list is intended to be of an exemplary and non-limiting nature. However, the fatty alcohols derive from preferably natural fatty acids, wherein it can conventionally be assumed that they are obtained from the esters of fatty acids by reduction. Likewise suitable for use according to the invention are fatty alcohol cuts constituting a mixture of different fatty alcohols. Such substances are available commercially for example under the names Stenol®, e.g. Stenol® 1618 or Lanette®, e.g. Lanette® O or Lorol®, e.g. Lorol® C8, Lorol® C14, Lorol® C18, Lorol® C8-18, HD-Ocenol®, Crodacol®, e.g. Crodacol® CS, Novol®, Eutanol® G, Guerbitol® 16, Guerbitol® 18, Guerbitol® 20, Isofol® 12, Isofol® 16, Isofol® 24, Isofol® 36, Isocarb® 12, Isocarb® 16 or Isocarb® 24. Wool wax alcohols can of course also be used according to the invention, such as are available commercially for example under the names Corona®, White Swan®, Coronet® or Fluilan®. The fatty alcohols are used in amounts from 0.1 to 30 wt. %, relative to the total preparation, preferably in amounts from 0.1 to 20 wt. %.

Solid paraffins or isoparaffins, carnauba waxes, beeswaxes, candelilla waxes, ozokerites, ceresin, spermaceti wax, sunflower wax, fruit waxes such as for example apple wax or citrus wax, PE or PP microwaxes can be used according to the invention as natural or synthetic waxes (Fatwax). Such waxes are available for example from Kahl & Co., Trittau.

The amount used is 0.1 to 50 wt. %, relative to the total agent, preferably 0.1 to 20 wt. % and particularly preferably 0.1 to 15 wt. %, relative to the total agent.

The total amount of oil and fat components in the agents according to the invention is conventionally 0.5 to 75 wt. %, relative to the total agent. Amounts from 0.5 to 35 wt % are preferred according to the invention.

Protein hydrolysates and/or derivatives thereof (P) are a further synergistic active agent according to the invention in the compositions according to the invention with the active agent complex according to the invention.

According to the invention protein hydrolysates of both plant and animal or marine or synthetic origin can be used.

Animal protein hydrolysates are for example elastin, collagen, keratin, silk and milk protein hydrolysates, which can also be present in the form of salts. Such products are sold for example under the trademarks Dehylan® (Cognis), Promois® (Interorgana), Collapuron® (Cognis), Nutrilan® (Cognis), Gelita-Sol® (Deutsche Gelatine Fabriken Stoess & Co), Lexein® (Inolex) and Kerasol® (Croda).

Also preferred according to the invention are plant protein hydrolysates, such as for example soy, almond, pea, moringa, potato and wheat protein hydrolysates. Such products are available for example under the trademarks Gluadin® (Cognis), DiaMin® (Diamalt), Lexein® (Inolex), Hydrosoy® (Croda), Hydrolupin® (Croda), Hydrosesame® (Croda), Hydrotritium® (Croda), Crotein® (Croda) and Puricare® LS 9658 from Laboratoires Sérobiologiques.

Further protein hydrolysates that are preferred according to the invention are of marine origin. They include for example collagen hydrolysates of fish or algae and protein hydrolysates of mussels or pearl hydrolysates. Examples of pearl extracts according to the invention are the commercial products Pearl Protein Extract BG® or Crodarom® Pearl.

The protein hydrolysates and derivatives thereof also include cationized protein hydrolysates, wherein the underlying protein hydrolysate can derive from animal sources, for example from collagen, milk or keratin, from plant sources, for example from wheat, corn, rice, potatoes, soy or almonds, from marine life forms, for example from fish collagen or algae, or from protein hydrolysates obtained by biotechnology. Typical examples of the cationic protein hydrolysates and derivatives according to the invention are the products that are listed under the INCI names in the "International Cosmetic Ingredient Dictionary and Handbook", (seventh edition 1997, The Cosmetic, Toiletry, and Fragrance Association, 1101 17th Street, N.W., Suite 300, Washington, DC 20036-4702) and that are available commercially.

The protein hydrolysates (P) are included in the compositions in concentrations from 0.001 wt. % to 20 wt. %, preferably from 0.05 wt. % to 15 wt. % and most particularly preferably in amounts from 0.05 wt. % to 5 wt. %.

A further preferred group of ingredients of the compositions according to the invention with the active agent complex according to the invention are vitamins, provitamins or vitamin precursors. Vitamins, provitamins and vitamin precursors are particularly preferably that are assigned to groups A, B, C, E, F and H.

The group of substances classed as vitamin A includes retinol (vitamin $A_1$) and 3,4-didehydroretinol (vitamin $A_2$). β-Carotene is the retinol provitamin. Suitable vitamin A components according to the invention are for example vitamin A acid and esters thereof, vitamin A aldehyde and vitamin A alcohol and esters thereof such as the palmitate and acetate. The agents according to the invention include the vitamin A component preferably in amounts from 0.05 to 1 wt. %, relative to the total preparation.

The vitamin B group or vitamin B complex includes inter alia:

Vitamin $B_1$ (thiamine)

Vitamin $B_2$ (riboflavin)

Vitamin $B_3$. The compounds nicotinic acid and nicotinic acid amide (niacinamide) are often included under this term. Preferred according to the invention is nicotinic acid amide, which is preferably included in the agents used according to the invention in amounts from 0.05 to 1 wt. %, relative to the total agent.

Vitamin $B_5$ (pantothenic acid, panthenol and pantolactone). Within the context of this group panthenol and/or pantolactone is preferably used. Derivatives of panthenol which can be used according to the invention are in particular the esters and ethers of panthenol as well as cationically derivatized panthenols. Individual representatives are for example panthenol triacetate, panthenol monoethyl ether and the monoacetate thereof, and cationic panthenol derivatives. Pantothenic acid is preferably used in the present invention as a derivative in the form of the more stable calcium salts and sodium salts (Ca pantothenate, Na pantothenate).

Vitamin $B_6$ (pyridoxine as well as pyridoxamine and pyridoxal).

The cited compounds of the vitamin B type, in particular vitamin $B_3$, $B_5$ and $B_6$, are included in the agents according to the invention preferably in amounts from 0.05 to 10 wt. %, relative to the total agent. Amounts from 0.1 to 5 wt. % are particularly preferred.

Vitamin C (ascorbic acid). Vitamin C is used in the agents according to the invention preferably in amounts from 0.1 to 3 wt. %, relative to the total agent. Use in the form of the palmitic acid ester, glucosides or phosphates can be preferred. Use in combination with tocopherols can likewise be preferred.

Vitamin E (tocopherols, in particular α-tocopherol). Tocopherol and derivatives thereof, which include in particular esters such as acetate, nicotinate, phosphate and succinate, are preferably included in the agents according to the invention in amounts from 0.05 to 1 wt. %, relative to the total agent.

Vitamin F. The term "vitamin F" is conventionally understood to mean essential fatty acids, in particular linoleic acid, linolenic acid and arachidonic acid.

Vitamin H. Vitamin H is the name given to the compound (3aS,4S, 6aR)-2-oxohexahydrothienol[3,4-d]-imidazole-4-valeric acid, although this is now more widely known by the trivial name biotin. Biotin is preferably included in the agents according to the invention in amounts from 0.0001 to 1.0 wt. %, in particular in amounts from 0.001 to 0.01 wt. %.

The compositions according to the invention preferably include vitamins, provitamins and vitamin precursors from groups A, B, E and H. Panthenol, pantolactone, pyridoxine and derivatives thereof as well as nicotinic acid amide and biotin are particularly preferred.

A particularly preferred group of ingredients in the cosmetic compositions according to the invention is constituted by the betaines listed below: carnitine, carnitine tartrate, carnitine magnesium citrate, acetyl carnitine, betalains, 1,1-dimethyl proline, choline, choline chloride, choline bitartrate, choline dihydrogen citrate and the compound N,N,N-trimethylglycine, which is classed in the literature as betaine.

Carnitine, histidine, choline and betaine are preferably used. In a particularly preferred embodiment of the invention L-carnitine tartrate is used as the active agent.

Agents according to the invention which include—relative to their weight—0.0001 to 10.0 wt. %, preferably 0.0005 to 5.0 wt. %, particularly preferably 0.001 to 2.0 wt. % and in particular 0.001 to 1.0 wt. % of at least one of the aforementioned betaines, in particular carnitine tartrate, are particularly preferred.

In a further embodiment that is preferred according to the invention the compositions according to the invention include bioquinones. In the agents according to the invention suitable bioquinones are understood to be one or more ubiquinones and/or plastoquinones. The ubiquinones that are preferred according to the invention have the following formula:

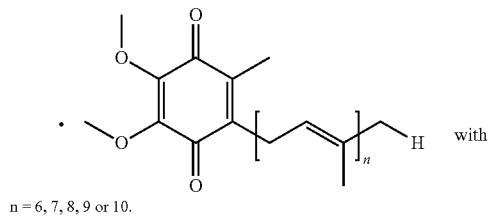

n = 6, 7, 8, 9 or 10.

Coenzyme Q-10 is most preferred here.

Preferred compositions according to the invention include purine and/or purine derivatives in relatively narrow quantity ranges. Cosmetic agents that are preferred according to the invention are characterized in that they include—relative to their weight —0.001 to 2.5 wt. %, preferably 0.0025 to 1 wt. %, particularly preferably 0.005 to 0.5 wt. % and in particular 0.01 to 0.1 wt. % of purine(s) and/or purine derivative(s). Cosmetic agents that are preferred according to the invention are characterized in that they include purine, adenine, guanine, uric acid, hypoxanthine, 6-purinethiol, 6-thioguanine, xanthine, caffeine, theobromine or theophylline. In hair cosmetics preparations caffeine is most preferred.

In a further preferred embodiment of the present invention the cosmetic agent includes ectoine ((S)-2-methyl-1,4,5,6-tetrahydro-4-pyrimidine carboxylic acid).

Particularly preferred according to the invention are agents which include—relative to their weight—0.00001 to 10.0 wt. %, preferably 0.0001 to 5.0 wt % and in particular 0.001 to 3 wt. % of active agents from the group formed from carnitine, coenzyme Q-10, ectoine, a vitamin of the B series, a purine and derivatives or physiologically acceptable salts thereof.

A most particularly preferred care additive in the hair treatment agents according to the invention is taurine. Taurine is understood to be exclusively 2-aminoethane sulfonic acid, and a derivative to be the explicitly cited taurine derivatives. The taurine derivatives are understood to be N-monomethyltaurine, N,N-dimethyltaurine, taurine lysylate, taurine tartrate, taurine ornithate, lysyl taurine and ornithyl taurine.

Agents according to the invention which include—relative to their weight—0.0001 to 10.0 wt. %, preferably 0.0005 to 5.0 wt. %, particularly preferably 0.001 to 2.0 wt. % and in particular 0.001 to 1.0 wt. % of taurine and/or a taurine derivative are particularly preferred.

The effect of the compositions according to the invention can be further increased by means of a 2-pyrrolidinone-5-carboxylic acid and derivatives (J) thereof. The sodium, potassium, calcium, magnesium or ammonium salts are preferred, in which the ammonium ion bears one to three $C_1$ to $C_4$ alkyl groups in addition to hydrogen. The sodium salt is most particularly preferred. The amounts used in the agents according to the invention are 0.05 to 0.10 wt. %, relative to the total agent, particularly preferably 0.1 to 5, and in particular 0.1 to 3 wt. %.

Through the use of plant extracts as care substances the hair treatment agents according to the invention can be formulated so that they are particularly close to nature and yet very effective in their care performance. Preservatives that are otherwise conventionally used can even optionally be dispensed with. Preferred above all according to the invention are the extracts from green tea, oak bark, stinging nettle, witch hazel, hops, henna, chamomile, burdock, horsetail, whitethorn, lime blossom, almond, aloe vera, pine, horse chestnut, sandalwood, juniper, coconut, mango, apricot, lemon, wheat, kiwi, melon, orange, grapefruit, sage, rosemary, birch, mallow, valerian, lady's smock, wild thyme, yarrow, thyme, melissa, restharrow, coltsfoot, marshmallow, meristem, *ginseng*, coffee, cocoa, moringa, ginger root and ayurvedic plant extracts such as for example *Aegle marmelos* (bilva), *Cyperus rotundus* (nagarmotha), *Emblica officinalis* (amalaki), *Morinda citrifolia* (ashyuka), *Tinospora cordifolia* (guduchi), *Santalum album* (chandana), *Crocus sativus* (kumkuma), *Cinnamonum zeylanicum* and *Nelumbo nucifera* (kamala), grasses such as wheat, barley, rye, oats, spelt, corn, the various types of millet (proso millet, finger millet, foxtail millet as examples), sugar cane, ryegrass, meadow foxtail, false oat-grass, bentgrass, meadow fescue, moor grass, bamboo, cottongrass, pennisetums, Andropogonodeae (*Imperata cylindrica*, also known as blood grass or cogon grass), buffalo grass, cord grass, dog's tooth grass, lovegrass, *Cymbopogon* (citronella grass), *Oryzeae* (rice), *Zizania* (wild rice), marram grass, blue oatgrass, soft-grass, quaking grasses, speargrass, couch grass and *Echinacea*, in particular *Echinacea purpurea* (L.) Moench, all types of vine and pericarp of *Litchi chinensis*.

The plant extracts can be used according to the invention in both pure and diluted form. If they are used in diluted form they conventionally include approximately 2 to 80 wt. % of active substance and as the solvent the extracting agent or mixture of extracting agents used to obtain them.

It can occasionally be necessary to use anionic polymers. Examples of anionic monomers which can constitute such polymers are acrylic acid, methacrylic acid, crotonic acid, maleic anhydride and 2-acrylamido-2-methylpropane sulfonic acid. Some or all of the acid groups therein can be present as the sodium, potassium, ammonium, mono- or triethanolammonium salt. Preferred monomers are 2-acrylamido-2-methylpropane sulfonic acid and acrylic acid.

Anionic polymers that include as the sole monomer or as a co-monomer 2-acrylamido-2-methylpropane sulfonic acid, in which some or all of the sulfonic acid group can be present as the sodium, potassium, ammonium, mono- or triethanolammonium salt, have proved to be most particularly effective.

The homopolymer of 2-acrylamido-2-methylpropane sulfonic acid, which is available commercially for example under the name Rheothik 11-80, is particularly preferred.

Preferred non-ionogenic monomers are acrylamide, methacrylamide, acrylic acid ester, methacrylic acid ester, vinylpyrrolidone, vinyl ether and vinyl ester.

Preferred anionic copolymers are acrylic acid-acrylamide copolymers as well as in particular polyacrylamide copolymers with monomers that include sulfonic acid groups. Such a polymer is included in the commercial product Sepigel® 305 from SEPPIC.

Likewise preferred anionic homopolymers are uncrosslinked and crosslinked polyacrylic acids. Allyl ethers of pentaerythritol, of sucrose and of propylene can be preferred crosslinking agents here. Such compounds are available commercially for example under the trademark Carbopol®.

Copolymers of maleic anhydride and methyl vinyl ether, in particular those with crosslinkages, are likewise color-retaining polymers. A maleic acid-methyl vinyl ether copolymer crosslinked with 1,9-decadiene is available commercially under the name Stabileze® QM.

The anionic polymers are included in the agents according to the invention preferably in amounts from 0.05 to 10 wt. %, relative to the total agent. Amounts from 0.1 to 5 wt. % are particularly preferred.

In a further embodiment the agents according to the invention can include non-ionogenic polymers.

Suitable non-ionogenic polymers are for example:

vinylpyrrolidone/vinyl ester copolymers, such as are sold for example under the trademark Luviskol® (BASF). Luviskol® VA 64 and Luviskol® VA 73, both of which are vinylpyrrolidone/vinyl acetate copolymers, are likewise preferred non-ionic polymers;

cellulose ethers, such as hydroxypropylcellulose, hydroxyethylcellulose and methylhydroxypropyl cellulose, such as are sold for example under the trademarks Culminal® and Benecel® (AQUALON), and Natrosol® types (Hercules);

starch and derivatives thereof, in particular starch ethers, for example Structure® XL (National Starch), a multifunctional, salt-tolerant starch;

shellac;

polyvinylpyrrolidones, such as are sold for example under the name Luviskol® (BASF).

The non-ionic polymers are included in the compositions according to the invention preferably in amounts from 0.05 to 10 wt. %, relative to the total agent. Amounts from 0.1 to 5 wt. % are particularly preferred.

The cosmetic agents can furthermore include additional active agents, auxiliary substances and additives, such as for example texturizing agents such as maleic acid and lactic acid, swelling agents such as urea, allantoin, carbonates or hydantoin, dimethyl isosorbide and cyclodextrins, dyes to color the agent, anti-dandruff active agents such as piroctone olamine, zinc omadine and climbazole, complexing agents such as EDTA, NTA, β-alanine diacetic acid and phosphonic acids, opacifiers such as latex, styrene/PVP and styrene/acrylamide copolymers, pearlescent agents such as ethylene glycol mono- and distearate as well as PEG-3 distearate, pigments, stabilizing agents for hydrogen peroxide and other oxidizing agents, blowing agents such as propane-butane mixtures, $N_2O$, dimethyl ether, $CO_2$ and air, antioxidants, perfume oils, scents and fragrances.

With regard to further optional components and to the amounts of these components used, reference is expressly made to the relevant manuals known to the person skilled in the art.

The invention secondly provides a method for hair treatment, in which a hair treatment agent according to claim 1 is applied to the hair and is rinsed out of the hair after a contact period.

The contact period is preferably a few seconds to 100 minutes, particularly preferably 1 to 50 minutes and most particularly preferably 1 to 30 minutes.

A method in which a cosmetic agent according to claim 1 is applied to the hair and remains there is also in accordance with the invention. "Remains on the hair" is understood to mean according to the invention that the agent is not rinsed out of the hair again immediately after being applied. In this case the agent instead remains on the hair for more than 100 minutes and up until the next time the hair is washed.

The following examples are intended to illustrate the subject matter of the present invention without however limiting its scope.

EXAMPLES

Unless otherwise specified, all stated amounts are parts by weight. The following formulations were prepared using known production methods.

Hair Rinse:

| | R1 | R2 | R3 | R4 | R5 | R6 |
|---|---|---|---|---|---|---|
| Stenol ® 1618 | 3.0 | 3.0 | 3.0 | 3.0 | 3.0 | 3.0 |
| Genamin ® KDMP | 2.0 | — | 2.0 | — | — | — |
| Cetrimonium chloride | — | — | — | — | 1.0 | — |
| Rheocare ® Ultragel | 2.0 | — | — | — | — | — |
| Dehyquart ® L80 | 0.5 | — | — | 0.5 | — | — |
| Polyquaternium-77 | 0.5 | — | — | 0.5 | — | — |
| Silcare ® SEA | 0.5 | — | 0.5 | — | — | — |
| Polyquaternium-71 | 0.5 | — | 0.5 | — | — | — |
| Terraquat ® BD | — | 3.0 | 0.5 | — | 3.0 | 1.0 |
| Dow Corning ® 949 | — | — | — | 0.5 | — | — |
| Stearyldimoniumhydroxypropyl laurylglucoside | 0.5 | — | 0.5 | 0.5 | — | — |
| Bis-(Ethyl(isostearylimidazoline) isostearamide | 1.0 | 1.0 | 1.0 | 1.0 | 1.0 | 1.0 |
| CDHP* | 1.0 | 1.0 | 1.0 | 1.0 | 1.0 | 1.0 |
| Panthenol | 0.5 | 0.5 | 0.3 | 0.5 | 0.2 | 0.2 |
| Isopropyl myristate | 0.4 | — | — | — | — | — |
| DC ® 200, 60,000 cSt | 0.3 | — | 0.2 | — | — | — |
| Dicaprylyl carbonate | 0.3 | — | 0.3 | 0.3 | — | — |
| Titanium dioxide | 0.1 | — | — | — | 0.2 | 0.5 |
| Citric acid | — | — | — | 0.3 | — | — |
| Vanillic acid | 0.2 | 0.2 | — | 0.2 | — | — |
| Mandelic acid | — | — | 0.3 | 0.2 | 0.3 | — |
| Methylparaben | 0.2 | 0.2 | 0.2 | 0.2 | 0.2 | 0.2 |
| Perfume | 0.3 | 0.3 | 0.3 | 0.3 | 0.3 | 0.3 |
| Phenoxyethanol | 0.4 | 0.4 | 0.4 | 0.4 | 0.4 | 0.4 |
| Water | to 100 | to 100 | to 100 | to 100 | to 100 | to 100 |

*Cetearamidoethyl diethonium hydrolyzed protein

The pH values of all formulations were set to 2 to 4.

Hair Mask:

| | M1 | M2 | M3 | M4 | M5 | M6 |
|---|---|---|---|---|---|---|
| Stenol ® 1618 | 6.0 | 6.0 | 6.0 | 6.0 | 6.0 | 6.0 |
| Quartamin ® BTC 131 | 1.5 | — | 0.8 | 1.0 | — | — |
| Crodazosoft ® DBQ | 1.5 | — | — | 1.5 | — | — |
| Rheocare ® Ultragel | 3.0 | — | — | — | — | — |
| Dehyquart ® L80 | 0.5 | — | — | 0.5 | — | — |
| Dehyquart ® F 75 | — | — | — | — | 1.0 | — |
| Polyquaternium-77 | 0.5 | — | — | 0.5 | — | — |
| Silcare ® SEA | 0.5 | 0.5 | 0.5 | — | — | — |
| Polyquaternium-71 | 0.5 | — | 0.5 | — | — | — |
| Terraquat ® BD | — | 4.5 | 0.5 | 1.5 | 4.5 | 1.5 |
| Dow Corning ® 949 | — | — | — | 0.5 | — | — |
| Stearyldimoniumhydroxypropyl laurylglucoside | 0.5 | — | 0.5 | 0.5 | | |
| Bis-(Ethyl(isostearylimidazoline) isostearamide | 1.0 | 1.5 | 4.0 | 3.0 | 1.5 | 1.5 |
| CDHP* | 1.0 | 1.0 | 1.0 | 1.0 | 1.0 | 1.0 |
| Benzophenone-4 | 0.5 | — | — | — | 2.0 | 1.0 |
| Citric acid | — | — | — | 0.3 | — | — |
| Vanillic acid | 2.0 | 2.0 | — | 0.5 | — | — |
| Mandelic acid | — | — | 0.3 | 2.0 | 0.3 | — |
| Isopropyl myristate | 0.4 | — | 0.4 | — | — | — |
| Panthenol | 0.5 | 0.5 | 0.8 | 0.5 | 0.5 | 0.5 |
| DC ® 200, 60,000 cSt | 0.3 | — | 0.2 | — | — | — |
| Cetiol ® C5 | 1.0 | — | 0.3 | 0.3 | — | — |
| Dicaprylyl carbonate | 0.3 | — | 0.3 | 0.3 | — | — |
| Methylparaben | 0.2 | — | 0.2 | 0.2 | 0.2 | 0.2 |
| Perfume | 0.3 | 0.3 | 0.3 | 0.3 | 0.3 | 0.3 |
| Phenoxyethanol | 0.4 | 0.4 | 0.4 | 0.4 | 0.4 | 0.4 |
| Water | to 100 | to 100 | to 100 | to 100 | to 100 | to 100 |

*Cetearamidoethyl diethonium hydrolyzed protein

The pH values of all formulations were set to 2 to 4.

Hair Shampoo:

| | HS1 | HS2 | HS3 | HS4 | HS5 |
|---|---|---|---|---|---|
| Ammonium lauryl ether sulfate (2-EO) | 20.0 | 20.0 | 9.0 | — | — |
| Sodium lauryl ether sulfate (2-EO) | — | — | — | 9.0 | 9.0 |
| Terraquat ® BD | 2.0 | 2.0 | — | — | — |
| Ammonium lauryl sulfate (30%) | 20.0 | 20.0 | — | — | — |
| Cocamidopropyl betaine | 7.0 | 7.0 | 3.0 | 3.0 | 3.0 |
| Plantacare ® 818 UP | — | — | 6.0 | 6.0 | 6.0 |
| Sodium benzoate | 0.2 | 0.2 | 0.2 | 0.2 | 0.2 |
| Citric acid or lactic acid or a mixture of both | 1.0 | 1.0 | 1.0 | 1.0 | 1.0 |
| Thickening agent | 1.0 | 2.0 | 0.5 | 2.5 | 1.0 |
| CDHP* | 1.0 | 1.0 | 1.0 | 1.0 | 1.0 |
| Polyquaternium-77 | 0.5 | — | — | 0.5 | — |
| Silcare ® SEA | 0.5 | — | 0.5 | — | 0.3 |
| Cosmedia ® Guar C261 | — | — | — | 0.4 | — |
| Polyquaternium-71 | 0.5 | — | 0.5 | — | 0.1 |
| Polyquaternium-74 | — | — | 03 | — | 0.2 |
| Dow Corning ® 949 | — | — | — | 0.5 | — |
| Stearyldimoniumhydroxypropyl laurylglucoside | 0.5 | — | 0.5 | 0.5 | 0.5 |
| Bis-(Ethyl(isostearylimidazoline) isostearamide | 2.0 | 2.0 | 3.0 | 4.0 | 1.0 |
| Benzophenone-4 | — | 0.5 | 0.8 | 0.8 | — |
| Titanium dioxide | 0.2 | — | — | 0.2 | 0.8 |
| Lactic acid | 0.5 | — | — | — | 2.0 |
| Citric acid | — | — | — | 0.3 | — |
| Vanillic acid | 2.0 | 2.0 | — | 0.5 | — |
| Mandelic acid | — | — | 0.3 | 2.0 | 0.3 |
| Isopropyl myristate | 0.4 | — | 0.4 | — | — |
| Panthenol | 0.5 | 0.5 | 0.8 | 0.5 | 0.5 |
| DC ® 200, 60,000 cSt | 0.3 | — | 0.2 | — | — |
| Cetiol ® C5 | 1.0 | — | 0.3 | 0.3 | — |
| Dicaprylyl carbonate | 0.3 | — | 0.3 | 0.3 | — |

-continued

|  | HS1 | HS2 | HS3 | HS4 | HS5 |
|---|---|---|---|---|---|
| Perfume | 0.3 | 0.3 | 0.3 | 0.3 | 0.3 |
| Phenoxyethanol | 0.4 | 0.4 | 0.4 | 0.4 | 0.4 |
| Water | to 100 | to 100 | to 100 | to 100 | to 100 |

*Cetearamidoethyl diethonium hydrolyzed protein

The pH values of all formulations were set to 4.5 to 5.8.

All thickening agents or thickening agent systems known to the person skilled in the art in surfactant systems can be used as the thickening agent. Celluose ethers, xanthan gums, hydroxyethylcelluloses, laureth-2 and laureth-3, for example, as well as the products available under the trade name Antil® or Crothix®, for example, can be used particularly advantageously in the aforementioned formulations, in each case either individually or in mixtures with one another.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

What is claimed is:

1. A hair treatment agent including—relative to its weight—
   a) at least one selected complex of an acid protein hydrolysate and a basic fatty acid amidoamine in a total amount from 1.0 to 10.0 wt. %, relative to the total composition, the acid protein hydrolysate being selected from the group consisting of plant based protein hydrolysates, collagen hydrolysates, keratin hydrolysates, silk hydrolysates, and milk protein hydrolysates, and the basic fatty acid amidoamine having the structure $R^1$—$NR^2$—$(CH_2)_n$—$NR^3R^4R^5$, in which $R^1$ denotes a linear or branched, saturated or unsaturated acyl residue with 8 to 40 C atoms in the chain, $R^2$ denotes a $C_1$ to $C_4$ alkyl residue or hydrogen, $R^3$, $R^4$ and $R^5$ mutually independently denote hydrogen, a methyl residue or a $C_2$ to $C_4$ alkyl residue, n denotes an integer selected from 1, 2, 3, 4 or 5, and b) at least one UV filter in a total amount from 0.01 to 15.0 wt. %, relative to the total composition, and
   c) 0.1 to 15.0 wt. % esterquats.

2. A hair treatment agent including—relative to its weight—
   a) at least one cetearamidoethyl diethonium hydrolyzed protein in a total amount from 1.0 to 10.0 wt. %, relative to the total composition, and
   b) at least one UV filter in a total amount from 0.01 to 15.0 wt. %, relative to the total composition, and
   c) 0.1 to 15.0 wt. % esterquats.

3. The hair treatment agent according to claim 1, further including at least one silicone compound.

4. The hair treatment agent according to claim 3, wherein the silicone is an amino-functional silicone.

5. The hair treatment agent according to claim 1, further including carnitine.

6. The hair treatment agent according to claims 1, further including a purine.

7. The hair treatment agent according to claim 1, further including ectoine.

8. The hair treatment agent according to claim 1, further including at least one ubiquinone.

9. A method for treating keratinic fibers, including applying a hair treatment agent according to claim 1 to the keratinic fibers, and rinsing the agent out after a contact time of a few seconds up to 45 minutes.

10. The hair treatment agent according to claim 2, further including at least one silicone compound.

11. The hair treatment agent according to claim 10, wherein the silicone is an amino-functional silicone.

12. The hair treatment agent according to claim 2, further including carnitine.

13. The hair treatment agent according to claims 2, further including a purine.

14. The hair treatment agent according to claim 2, further including ectoine.

15. The hair treatment agent according to claim 2, further including at least one ubiquinone.

16. A method for treating keratinic fibers, including applying a hair treatment agent according to claim 2 to the keratinic fibers, and rinsing the agent out after a contact time of a few seconds up to 45 minutes.

* * * * *